(12) United States Patent
Fayol et al.

(10) Patent No.: US 8,507,476 B2
(45) Date of Patent: Aug. 13, 2013

(54) SUBSTITUTED ARYLAMIDE DIAZEPINOPYRIMIDONE DERIVATIVES

(75) Inventors: Aude Fayol, Paris (FR); Alistair Lochead, Paris (FR); Mourad Saady, Paris (FR); Julien Vache, Paris (FR); Philippe Yaiche, Paris (FR)

(73) Assignees: Sanofi, Paris (FR); Mitsubishi Tanabe Pharma Corporation, Osaka (JP)

( * ) Notice: Subject to any disclaimer, the term of this patent is extended or adjusted under 35 U.S.C. 154(b) by 346 days.

(21) Appl. No.: 12/844,278

(22) Filed: Jul. 27, 2010

(65) Prior Publication Data
US 2011/0039835 A1 Feb. 17, 2011

Related U.S. Application Data

(63) Continuation of application No. PCT/IB2009/000324, filed on Jan. 27, 2009.

(30) Foreign Application Priority Data

Jan. 29, 2008 (EP) .................................... 08290074

(51) Int. Cl.
*A61P 25/00* (2006.01)
*A61K 31/55* (2006.01)
*C07D 491/00* (2006.01)

(52) U.S. Cl.
USPC .......................................... 514/221; 540/568

(58) Field of Classification Search
USPC .......................................... 514/221; 540/568
See application file for complete search history.

(56) References Cited

U.S. PATENT DOCUMENTS

| | | | |
|---|---|---|---|
| 4,104,386 A | 8/1978 | Barreau et al. | |
| 2003/0096813 A1 | 5/2003 | Cao et al. | |
| 2004/0266793 A1 | 12/2004 | Gallet et al. | |
| 2011/0015176 A1 | 1/2011 | Fayol et al. | |
| 2011/0015177 A1 | 1/2011 | Fayol et al. | |
| 2011/0015187 A1 | 1/2011 | Fayol et al. | |

FOREIGN PATENT DOCUMENTS

| | | |
|---|---|---|
| DE | 27 05 582 | 8/1977 |
| EP | 1 557 417 A1 | 7/2005 |
| EP | 1 790 649 A1 | 5/2007 |
| WO | WO 96/14844 | 5/1996 |
| WO | WO 97/16430 | 5/1997 |

OTHER PUBLICATIONS

International Search Report for WO2009/095789 dated Aug. 6, 2009.
Woodgett, Use of Peptide Substrates for Affinity Purification of Protein-Serine Kinases, Analytical Biochem., 1989 (180) pp. 237-241.
Bhat et al, Glycogen Synthase Kinase 3B: A drug Target for CNS Therapies, Journal of Neurochemistry, 2004 (89) pp. 1313-1317.
Carmichael et al, Glycogen Synthase Kinase-3B Inhibitors Prevent Cellular Polyglutamine Toxicity Caused by the Huntington's Disease Mutation, The Journal of Biological Chemistry, 2002 (277)37 pp. 33791-33798.
Chang et al, A Synthesis of Racemic Thalidomide, Synthetic Comm., 2003 (33)8 pp. 1375-1382.
Cohen et al, GSK3 Inhibitors: Development and Therapeutic Potential, Nature Reviews, 2004 (3) pp. 479-487.
Droucheau et al, *Plasmodium falciparum* Glycogen Synthase Kinase-3: Molecular Model, Expression, Intracellular Localisation and Selective Inhibitors, Biochimica et Biophysica Acta, 2004 (1697) pp. 181-196.
Koh et al, Role of GSK-3B Activity in Motor Neuronal Cell Death Induced by G93A or A4V Mutant hSOD1 Gene, European Journal of Neuroscience, 2005 (22) pp. 301-309.
Kypta, GSK-3 Inhibitors and Their Potential in the Treatment of Alzheimer's Disease, Expert Opin. Ther. Patents, 2005 (15) 10 pp. 1315-1331.
Martinez et al, Glycogen Synthase Kinase 3 (GSK-3) Inhibitors as New Promising Drugs for Diabetes, Neurodegeneration, Cancer, and Inflammation, Med. Res. Rev., 2002 (22)4 pp. 373-384.
Meijer et al, Pharmacological Inhibitors of Glycogen Synthase Kinase 3, Trends in Pharmacological Sciences, 2004 (25)9 pp. 471-480.
Merour et al, New Synthesis of (+/−)-2-Piperazinecarboxylic Acid, Tetrahedron Lett, 1991 (32) 22 pp. 2469-2470.
Obligado et al, CDK/GSK-3 Inhibitors as Therapeutic Agents for Parenchymal Renal Diseases, Kidney Int'l, 2008 (73) pp. 684-690.
Perez et al, Prion Peptide Induces Neuronal Cell Death Through a Pathway Involving Glycogen Synthase Kinase 3, Biochem. J., 2003 (372) pp. 129-136.
Rinaldi-Carmona et al, SR147778 [5-(4-Bromophenyl)-1-(2,4-Dichlorophenyl)-4-ethyl-N-(1-Piperidinyl)-1H-Pyrazole-3-Carboxamide], A New Potent and Selective Antagonist of the CB1 Cannabinoid Receptor: Biochemical and Pharmacological Characterization, The Journal of Pharmacology and Experimental Therapeutics, 2004 (310) 3 pp. 905-914.

(Continued)

*Primary Examiner* — Brenda Coleman
(74) *Attorney, Agent, or Firm* — Kelly L. Bender

(57) ABSTRACT

The disclosure relates to a series pyrimidone derivatives represented by formula (I) or a salt thereof, or a solvate thereof or a hydrate thereof:

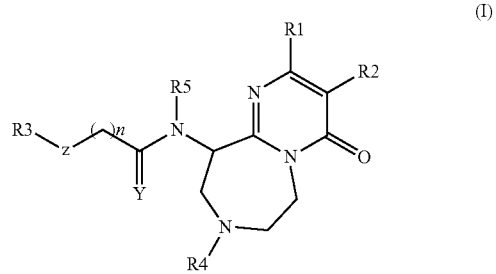

wherein:
Y, Z, R1, R2, R3, R4, R5 and n are as defined in the disclosure.
Also disclosed are methods of preparing the compounds of formula (I), intermediates therefor and their utility in treating a variety of disease conditions.

12 Claims, No Drawings

(56) References Cited

OTHER PUBLICATIONS

Sato et al, Maintenance of Pluripotency in Human and Mouse Embryonic Stem Cells Through Activation of Wnt Signaling by a Pharmacological GSK-3-Specific Inhibitor, Nature Medicine, 2004 (10) pp. 55-63.

Shankaran et al, Synthesis of analogs of (1,4)-3- and 5-imino oxazepane, thiazepane, and diazepane as inhibitors of nitric oxide synthases, Bioorganic & Med. Chem. Ltrs. (2004) 14 pp. 5907-5911.

Thenappan et al, An Expedient Synthesis of A-Fluoro-B-Ketoesters, Tetrahedron Letters, 1989 (30) 45 pp. 6113-6116.

Van Der Velden et al, Glycogen Synthase Kinase 3B Suppresses Myogenic Differentiation through Negative Regulation of NFAT c3, J. Biological Chem., 2008 (283) 1 pp. 358-366.

SUBSTITUTED ARYLAMIDE DIAZEPINOPYRIMIDONE DERIVATIVES

This application is a continuation of PCT/IB2009/000324, filed Jan. 27, 2009.

TECHNICAL FIELD

The present invention relates to compounds that are useful as an active ingredient of a medicament for preventive and/or therapeutic treatment of neurodegenerative diseases caused by abnormal activity of GSK3β.

BACKGROUND ART

GSK3β (glycogen synthase kinase 3β) is a proline directed serine, threonine kinase that plays an important role in the control of metabolism, differentiation and survival. It was initially identified as an enzyme able to phosphorylate and hence inhibit glycogen synthase. It was later recognized that GSK3β was identical to tau protein kinase 1 (TPK1), an enzyme that phosphorylates tau protein in epitopes that are also found to be hyperphosphorylated in Alzheimer's disease and in several taupathies. Interestingly, protein kinase B (AKT) phosphorylation of GSK3β results in a loss of its kinase activity, and it has been hypothesized that this inhibition may mediate some of the effects of neurotrophic factors. Moreover, phosphorylation by GSK3β of β-catenin, a protein involved in cell survival, results in its degradation by an ubiquitinilation dependent proteasome pathway.

Thus, it appears that inhibition of GSK3β activity may result in neurotrophic activity. Indeed there is evidence that lithium, an uncompetitive inhibitor of GSK3β, enhances neuritogenesis in some models and also increases neuronal survival, through the induction of survival factors such as Bcl-2 and the inhibition of the expression of proapoptotic factors such as p53 and Bax.

Recent studies have demonstrated that β-amyloid increases the GSK3β activity and tau protein phosphorylation. Moreover, this hyperphosphorylation as well as the neurotoxic effects of β-amyloid are blocked by lithium chloride and by a GSK3β antisense mRNA. These observations strongly suggest that GSK3β may be the link between the two major pathological processes in Alzheimer's disease: abnormal APP (Amyloid Precursor Protein) processing and tau protein hyperphosphorylation.

Although tau hyperphosphorylation results in a destabilization of the neuronal cytoskeleton, the pathological consequences of abnormal GSK3β activity are, most likely, not only due to a pathological phosphorylation of tau protein because, as mentioned above, an excessive activity of this kinase may affect survival through the modulation of the expression of apoptotic and antiapoptotic factors. Moreover, it has been shown that β-amyloid-induced increase in GSK3β activity results in the phosphorylation and, hence the inhibition of pyruvate dehydrogenase, a pivotal enzyme in energy production and acetylcholine synthesis.

Altogether these experimental observations indicate that GSK3β may find application in the treatment of the neuropathological consequences and the cognitive and attention deficits associated with Alzheimer's disease, as well as other acute and chronic neurodegenerative diseases and other pathologies where GSK3β is deregulated (Nature reviews Vol. 3, June 2004, p. 479-487; Trends in Pharmacological Sciences Vol. 25 No. 9, September 2004, p. 471-480; Journal of Neurochemistry 2004, 89, 1313-1317; Medicinal Research Reviews, Vol. 22, No. 4, 373-384, 2002).

The neurodegenerative diseases include, in a non-limiting manner, Parkinson's disease, tauopathies (e.g. Fronto temporal dementia, corticobasal degeneration, Pick's disease, progressive supranuclear palsy), Wilson's disease, Huntington's disease (The Journal of Biological Chemistry Vol. 277, No. 37, issue of September 13, pp. 33791-33798, 2002), Prion disease (Biochem. J. 372, p. 129-136, 2003) and other dementia including vascular dementia; acute stroke and other traumatic injuries; cerebrovascular accidents (e.g. age related macular degeneration); brain and spinal cord trauma; amyotrophic lateral sclerosis (European Journal of Neuroscience, Vol. 22, pp. 301-309, 2005) peripheral neuropathies; retinopathies and glaucoma. Recent studies have also shown that inhibition of GSK3β results in neuronal differentiation of embryonic stem cells (ESC) and support the renewal of human and mouse ESCs and the maintenance of their pluripotency. This suggests that inhibitors of GSK3β could have applications in regenerative medicine (Nature Medicine 10, p. 55-63, 2004).

Inhibitors of GSK3β may also find application in the treatment of other nervous system disorders, such as bipolar disorders (manic-depressive illness). For example lithium has been used for more than 50 years as a mood stabiliser and the primary treatment for bipolar disorder. The therapeutic actions of lithium are observed at doses (1-2 mM) where it is a direct inhibitor of GSK3β. Although the mechanism of action of lithium is unclear, inhibitors of GSK3β could be used to mimic the mood stabilising effects of lithium. Alterations in Akt-GSK3β signaling have also been implicated in the pathogenesis of schizophrenia.

In addition, inhibition of GSK3β could be useful in treating cancers, such as colorectal, prostate, breast, non-small cell lung carcinoma, thyroid cancer, T or B-cell leukaemia and several virus-induced tumours. For example, the active form of GSK3β has been shown to be elevated in the tumors of colorectal cancer patients and inhibition of GSK3β in colorectal cancer cells activates p53-dependent apoptosis and antagonises tumor growth. Inhibition of GSK3β also enhances TRAIL-induced apoptosis in prostate cancer cell lines. GSK3β also plays a role in the dynamics of the mitotic spindle and inhibitors of GSK3β prevent chromosome movement and lead to a stabilisation of microtubules and a prometaphase-like arrest that is similar to that observed with low doses of Taxol. Other possible applications for GSK3β inhibitors include therapy for non-insulin dependent diabetes (such as diabetes type II), obesity and alopecia.

Inhibitors of human GSK3β may also inhibit pfGSK3, an ortholog of this enzyme found in *Plasmodium falciparum*, as a consequence they could be used for the treatment of malaria (Biochimica et Biophysica Acta 1697, 181-196, 2004). Recently, both human genetics and animal studies have pointed out the role of Wnt/LPR5 pathway as a major regulator of bone mass accrual. Inhibition of GSK3β leads to the consequent activation of canonical Wnt signalling. Because deficient Wnt signalling has been implicated in disorders of reduced bone mass, GSK3β inhibitors may also be used for treating disorders of reduced bone mass, bone-related pathologies, osteoporosis.

According to recent data, GSK3β inhibitors might be used in the treatment or prevention of Pemphigus vulgaris.

Recent studies show that GSK3beta inhibitor treatment improves neutrophil and megakaryocyte recovery. Therefore, GSK3beta inhibitors will be useful for the treatment of neutropenia induced by cancer chemotherapy.

Previous studies have shown that GSK3 activity decreases LTP, a electrophysiological correlate of memory consolidation, suggesting that inhibitor of this enzyme may have procognitive activity. Procognitive effects of the compound could find application for the treatment of memory deficits characteristic of Alzheimer's disease, Parkinson disease, age-associated memory impairment, mild cognitive impairment, brain trauma, schizophrenia and other conditions in which such deficits are observed.

Inhibitors of GSK3β may also find application in the treatment of parenchymal renal diseases (Nelson P J, Kidney International Advance online publication 19 dec 2007) and in the prevention or treatment of muscle atrophy (J. Biol. Chem. 283 2008, 358-366).

DISCLOSURE OF THE INVENTION

An object of the present invention is to provide compounds useful as an active ingredient of a medicament for preventive and/or therapeutic treatment of a disease caused by abnormal GSK3β activity, more particularly of neurodegenerative diseases. More specifically, the object is to provide novel compounds useful as an active ingredient of a medicament that enables prevention and/or treatment of neurodegenerative diseases such as Alzheimer's disease.

Thus, the inventors of the present invention have identified compounds possessing inhibitory activity against GSK3β. As a result, they found that compounds represented by the following formula (I) had the desired activity and were useful as an active ingredient of a medicament for preventive and/or therapeutic treatment of the aforementioned diseases.

The present invention thus provides as an object of the invention the pyrimidone derivatives represented by formula (I) or salts thereof, solvates thereof or hydrates thereof:

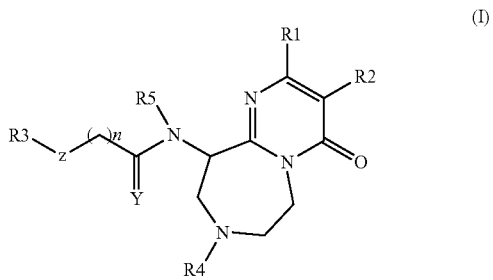

(I)

wherein:
Y represents two hydrogen atoms, a sulphur atom, an oxygen atom or a $C_{1-2}$ alkyl group and a hydrogen atom;
Z represents a bond, an oxygen atom, a nitrogen atom substituted by a hydrogen atom or a $C_{1-3}$ alkyl group, a sulphur atom, a methylene group optionally substituted by one or two groups chosen from a $C_{1-6}$ alkyl group, a hydroxyl group, a $C_{1-6}$ alkoxy group, a $C_{1-2}$ perhalogenated alkyl group or an amino group;
R1 represents a 2, 3 or 4-pyridine ring or a 2, 4 or 5-pyrimidine ring, the ring being optionally substituted by a $C_{1-6}$ alkyl group, a $C_{1-6}$ alkoxy group or a halogen atom;
R2 represents a hydrogen atom, a $C_{1-6}$ alkyl group or a halogen atom;
R3 represents a benzene ring or a naphthalene ring; the rings being optionally substituted by 1 to 4 substituents selected from a $C_{1-6}$ alkyl group, a halogen atom, a $C_{1-2}$ perhalogenated alkyl group, a $C_{1-3}$ halogenated alkyl group, a hydroxyl group, a $C_{1-6}$ alkoxy group, a $C_{1-2}$ perhalogenated alkoxy group, a $C_{1-6}$ alkylsulfonyl group, a nitro, a cyano, an amino, a $C_{1-6}$ monoalkylamino group, a $C_{2-12}$ dialkylamino group, an acetoxy group or an aminosulfonyl group, a 4-15 membered heterocyclic group, this group being optionally substituted by a $C_{1-6}$ alkyl group, a halogen atom, a $C_{1-2}$ perhalogenated alkyl group, a $C_{1-3}$ halogenated alkyl group, a hydroxyl group, a $C_{1-6}$ alkoxy group;
R4 represents a hydrogen atom; a $C_{1-6}$ alkyl group; a benzyl group, a phenethyl group, a benzyloxycarbonyl group, a $C_{1-4}$ alkoxy carbonyl group, a benzene group, a naphthalene group, a 5,6,7,8-tetrahydronaphthalene group, a benzenesulfonyl group, a benzoyl group, a 4-15 membered heterocyclic group, the above-mentioned group being optionally substituted by 1 to 4 substituents selected from a halogen atom, a hydroxyl group, a $C_{1-4}$ alkoxy group; a $C_{1-2}$ perhalogenated alkyl group, a $C_{1-6}$ alkyl group, a benzene group, a halogen atom, a $C_{1-3}$ halogenated alkyl group, a nitro, a cyano, an amino, a $C_{1-6}$ monoalkylamino group or a $C_{2-10}$ dialkylamino group;
R5 represents a hydrogen atom or a $C_{1-6}$ alkyl group; and n represents 0 to 3.

According to another aspect of the present invention, there is provided a medicament comprising as an active ingredient a substance selected from the group consisting of the pyrimidone derivatives represented by formula (I) and the physiologically acceptable salts thereof, and the solvates thereof and the hydrates thereof. As preferred embodiments of the medicament, there are provided the aforementioned medicament which is used for preventive and/or therapeutic treatment of diseases caused by abnormal GSK3β activity, and the aforementioned medicament which is used for preventive and/or therapeutic treatment of neurodegenerative diseases and in addition other diseases such as: Non-insulin dependent diabetes (such as diabetes type II) and obesity; malaria, bipolar disorders (manic depressive illness); schizophrenia; alopecia or cancers such as colorectal, prostate, breast cancer, non-small cell lung carcinoma, thyroid cancer, T or B-cell leukaemia, several virus-induced tumours and bone related pathologies; the treatment of parenchymal renal diseases and in the prevention or treatment of muscle atrophy; the treatment of cognitive and memory deficit. The medicament could also find an application in regenerative medicine.

As further embodiments of the present invention, there are provided the aforementioned medicament wherein the diseases are neurodegenerative diseases and are selected from the group consisting of Alzheimer's disease, Parkinson's disease, tauopathies (e.g. Fronto temporal dementia, corticobasal degeneration, Pick's disease, progressive supranuclear palsy), Wilson's disease, Huntington's disease, Prion disease and other dementia including vascular dementia; acute stroke and others traumatic injuries; cerebrovascular accidents (e.g. age related macular degeneration); brain and spinal cord trauma; amyotrophic lateral sclerosis; peripheral neuropathies; retinopathies and glaucoma, and the aforementioned medicament in the form of pharmaceutical composition containing the above substance as an active ingredient together with one or more pharmaceutical additives.

As further embodiments of the present invention, there are provided the aforementioned medicament wherein the bones related pathologies are osteoporosis.

The present invention further provides an inhibitor of GSK3β activity comprising as an active ingredient a substance selected from the group consisting of the pyrimidone derivatives of formula (I) and the salts thereof, and the solvates thereof and the hydrates thereof.

According to further aspects of the present invention, there is provided a method for preventive and/or therapeutic treatment of neurodegenerative diseases caused by abnormal GSK3β activity, which comprises the step of administering to a patient a preventively and/or therapeutically effective amount of a substance selected from the group consisting of pyrimidone derivatives of formula (I) and the physiologically acceptable salts thereof, and the solvates thereof and the hydrates thereof; and a use of a substance selected from the group consisting of the pyrimidone derivatives of formula (I) and the physiologically acceptable salts thereof, and the solvates thereof and the hydrates thereof for the manufacture of the aforementioned medicament.

As used herein, the $C_{1-6}$ alkyl group represents a straight or branched or cyclic alkyl group having 1 to 6 carbon atoms, optionally substituted by a straight, branched or cyclic $C_{1-6}$ alkyl group for example, methyl group, ethyl group, n-propyl group, isopropyl group, n-butyl group, isobutyl group, sec-butyl group, tert-butyl group, n-pentyl group, isopentyl group, neopentyl group, 1,1-dimethylpropyl group, n-hexyl group, isohexyl group, cyclopropylmethyl group and the like;

The $C_{1-6}$ alkoxy group represents an alkyloxy group having 1 to 4 carbon atoms for example, methoxy group, ethoxy group, propoxy group, isopropoxy group, butoxy group, isobutoxy group, sec-butoxy group, tert-butoxy group, and the like;

The halogen atom represents a fluorine, chlorine, bromine or iodine atom;

The $C_{1-2}$ perhalogenated alkyl group represents an alkyl group wherein all the hydrogen atoms have been substituted by a halogeno, for example a $CF_3$ or $C_2F_5$;

The $C_{1-3}$ halogenated alkyl group represents an alkyl group wherein at least one hydrogen has not been substituted by a halogen atom;

The $C_{1-6}$ monoalkylamino group represents an amino group substituted by one $C_{1-6}$ alkyl group, for example, methylamino group, ethylamino group, propylamino group, isopropylamino group, butylamino group, isobutylamino group, tert-butylamino group, pentylamino group, isopentylamino group and the like;

The $C_{2-12}$ dialkylamino group represents an amino group substituted by two $C_{1-6}$ alkyl groups, for example, dimethylamino group, ethylmethylamino group, diethylamino group, methylpropylamino group and diisopropylamino group and the like;

The 4-15 membered heterocyclic group represents an unsaturated, fully saturated or partially saturated mono- or polycyclic group (for example 4 to 10 members) containing one to seven heteroatoms chosen from N, O, and S. Examples of heterocyclic groups include pyridine, pyrindine, pyrimidine, pyrazine, pyridazine, triazine, pyrrole, furan, thiophene, pyrazole, imidazole, triazole, tetrazole, oxazole, isoxazole, oxadiazole, thiazole, isothiazole, thiadiazole, pyrrolopyrrole, pyrroloimidazole, pyrrolopyrazole, pyrrolotriazole, imidazoimidazole, imidazopyrazole, imidazotriazole, quinoline, isoquinoline, cinnoline, phthalazine, quinoxaline, quinazoline, naphthyridine, benzotriazine, pyridopyrimidine, pyridopyrazine, pyridopyridazine, pyridotriazine, pyrimidopyrimidine, pyrimidopyrazine, pyrimidopyridazine, pyrimidotriazine, pyrazinopyrazine, pyrazinopyridazine, pyrazinotriazine, pyridazinopyridazine, pyridazinotriazine, indole, isoindole, benzimidazole, indazole, indolizine, benzofuran, isobenzofuran, benzothiophene, benzo[c]thiophene, pyrrolopyridine, imidazopyridine, pyrazolopyridine, triazolopyridine, tetrazolopyridine, pyrrolopyrimidine, imidazopyrimidine, pyrazolopyrimidine, triazolopyrimidine, tetrazolopyrimidine, pyrrolopyrazine, imidazopyrazine, pyrazolopyrazine, triazolopyrazine, tetrazolopyrazine, pyrrolopyridazine, imidazopyridazine, pyrazolopyridazine, triazolopyridazine, tetrazolopyridazine, pyrrolotriazine, imidazotriazine, pyrazolotriazine, triazolotriazine, tetrazolotriazine, furopyridine, furopyrimidine, furopyrazine, furopyridazine, furotriazine, oxazolopyridine, oxazolopyrimidine, oxazolopyrazine, oxazolopyridazine, oxazolotriazine, isoxazolopyridine, isoxazolopyrimidine, isoxazolopyrazine, isoxazolopyridazine, isoxazolotriazine, oxadiazolopyridine, oxadiazolopyrimidine, oxadiazolopyrazine, oxadiazolopyridazine, oxadiazolotriazine, benzoxazole, benzisoxazole, benzoxadiazole, thienopyridine, thienopyrimidine, thienopyrazine, thienopyridazine, thienotriazine, thiazolopyridine, thiazolopyrimidine, thiazolopyrazine, thiazolopyridazine, thiazolotriazine, isothiazolopyridine, isothiazolopyrimidine, isothiazolopyrazine, isothiazolopyridazine, isothiazolotriazine, thiadiazolopyridine, thiadiazolopyrimidine, thiadiazolopyrazine, thiadiazolopyridazine, thiadiazolotriazine, benzothiazole, benzoisothiazole, benzothiadiazole, benzotriazole, benzodioxepine, benzodioxane, benzodioxine, diazepane. These heterocycles can exist also in a partially or fully saturated form, for example as an illustration dihydrobenzofuran, tetrahydroquinoline, etc. . . .

A leaving group L represents a group which could be easily cleaved and substituted; such a group may be for example a tosyl, a mesyl, a bromide and the like.

The compounds represented by the aforementioned formula (I) may form a salt. Examples of the salt include, when an acidic group exists, salts of alkali metals and alkaline earth metals such as lithium, sodium, potassium, magnesium, and calcium; salts of ammonia and amines such as methylamine, dimethylamine, trimethylamine, dicyclohexylamine, tris(hydroxymethyl)aminomethane, N,N-bis(hydroxyethyl)piperazine, 2-amino-2-methyl-1-propanol, ethanolamine, N-methylglucamine, and L-glucamine; or salts with basic amino acids such as lysine, δ-hydroxylysine and arginine. The base-addition salts of acidic compounds are prepared by standard procedures well known in the art.

When a basic group exists, examples include salts with mineral acids such as hydrochloric acid, hydrobromic acid; salts with organic acids such as acetic acid, propionic acid, tartaric acid, fumaric acid, maleic acid, malic acid, oxalic acid, succinic acid, citric acid, benzoic acid and the like.

The acid-addition salts of the basic compounds are prepared by standard procedures well known in the art which include, but are not limited thereto, dissolving the free base in an aqueous alcohol solution containing the appropriate acid and isolating the salt by evaporating the solution, or by reacting the free base and an acid in an organic solvent, in which case the salt separates directly, or is precipitated with a second organic solvent, or can be obtained by concentration of the solution. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial properties inherent in the free base are not compromised by side effects ascribable to the anions. Although medicinally acceptable salts of the basic compounds are preferred, all acid-addition salts are within the scope of the present invention.

In addition to the pyrimidone derivatives represented by the aforementioned formula (I) and salts thereof, their solvates and hydrates also fall within the scope of the present invention.

The pyrimidone derivatives represented by the aforementioned formula (I) may have one or more asymmetric carbon atoms. As for the stereochemistry of such asymmetric carbon atoms, they may independently be either (R) or (S) configuration, and the derivative may exist as stereoisomers such as optical isomers, or diastereoisomers. Any stereoisomers in pure form, any mixtures of stereoisomers, racemates and the like fall within the scope of the present invention.

Examples of compounds of the present invention are shown in table 1 hereinafter. However, the scope of the present invention is not limited by these compounds.

In a first embodiment of the invention, compounds of formula (I) wherein
Y represents an oxygen atom or two hydrogen atoms;
Z represents a bond;
R1 represents an unsubstituted 4-pyridine ring or unsubstituted 4-pyrimidine ring;
R2 represents an hydrogen atom;
R3 represents a benzene group optionally substituted by 1 to 4 substituents selected from a halogen atom, a $C_{1-3}$ perhalogenated alkyl group, a $C_{1-6}$ alkoxy group, an amino, a pyrazole group, an oxadiazole group, the oxadiazole group and the pyrazole group being optionally substituted by 1 to 4 substituents selected from a $C_{1-6}$ alkyl group;
R4 represents an hydrogen atom, a $C_{1-6}$ alkyl group, a COO ($C_{1-6}$-alkyl) group, a phenyl group, these group being eventually substituted by 1 to 3 halogen,
n represents 0,
in the form of a free base or of an addition salt with an acid.

A further object of the present invention includes the group of compounds of table 1 of formula as defined hereunder:
1. (+/−)-9-(4-Chloro-2-methoxy-benzoylamino)-4-oxo-2-pyrimidin-4-yl-5,6,8,9-tetrahydro-4H-1,4a,7-triaza-benzocycloheptene-7-carboxylic acid ethyl ester
2. (+/−)-4-Chloro-2-methoxy-N-(4-oxo-2-pyrimidin-4-yl-4,5,6,7,8,9-hexahydro-1,4a,7-triaza-benzocyclohepten-9-yl)-benzamide
3. (+/−)-4-Chloro-2-methoxy-N-(7-methyl-4-oxo-2-pyrimidin-4-yl-4,5,6,7,8,9-hexahydro-1,4a,7-triaza-benzocyclohepten-9-yl)-benzamide
4. (+/−)-4-Chloro-N-[7-(4-fluoro-phenyl)-4-oxo-2-pyrimidin-4-yl-4,5,6,7,8,9-hexahydro-1,4a,7-triaza-benzocyclohepten-9-yl]-2-methoxy-benzamide
5. (+/−)-4-Chloro-N-(7-cyclopropylmethyl-4-oxo-2-pyrimidin-4-yl-4,5,6,7,8,9-hexahydro-1,4a,7-triaza-benzocyclohepten-9-yl)-2-methoxy-benzamide
6. (+/−)-4-Chloro-N-(7-isopropyl-4-oxo-2-pyrimidin-4-yl-4,5,6,7,8,9-hexahydro-1,4a,7-triaza-benzocyclohepten-9-yl)-2-methoxy-benzamide
7. (+/−)-4-Chloro-N-(7-cyclopentyl-4-oxo-2-pyrimidin-4-yl-4,5,6,7,8,9-hexahydro-1,4a,7-triaza-benzocyclohepten-9-yl)-2-methoxy-benzamide
8. (+/−)-4-Fluoro-2-methoxy-N-(4-oxo-2-pyrimidin-4-yl-4,5,6,7,8,9-hexahydro-1,4a,7-triaza-benzocyclohepten-9-yl)-benzamide
9. (+/−)-2,4-Dimethoxy-N-(4-oxo-2-pyrimidin-4-yl-4,5,6,7,8,9-hexahydro-1,4a,7-triaza-benzocyclohepten-9-yl)-benzamide
10. (+/−)-4-Chloro-2-methoxy-N-(4-oxo-2-pyridin-4-yl-4,5,6,7,8,9-hexahydro-1,4a,7-triaza-benzocyclohepten-9-yl)-benzamide
11. (−)-4-Chloro-2-methoxy-N-(4-oxo-2-pyrimidin-4-yl-4,5,6,7,8,9-hexahydro-1,4a,7-triaza-benzocyclohepten-9-yl)-benzamide
12. (+)-4-Chloro-2-methoxy-N-(4-oxo-2-pyrimidin-4-yl-4,5,6,7,8,9-hexahydro-1,4a,7-triaza-benzocyclohepten-9-yl)-benzamide
13. (+/−)-9-(4-Methoxy-benzylamino)-4-oxo-2-pyrimidin-4-yl-5,6,8,9-tetrahydro-4H-1,4a,7-triaza-benzocycloheptene-7-carboxylic acid ethyl ester
14. (+/−)-9-(2,4-Dimethoxy-benzoylamino)-4-oxo-2-pyrimidin-4-yl-5,6,8,9-tetrahydro-4H-1,4a,7-triaza-benzocycloheptene-7-carboxylic acid ethyl ester
15. (−)-4-Chloro-2-methoxy-N-(7-methyl-4-oxo-2-pyrimidin-4-yl-4,5,6,7,8,9-hexahydro-1,4a,7-triaza-benzocyclohepten-9-yl)-benzamide
16. (+)-4-Chloro-2-methoxy-N-(7-methyl-4-oxo-2-pyrimidin-4-yl-4,5,6,7,8,9-hexahydro-1,4a,7-triaza-benzocyclohepten-9-yl)-benzamide
17. (+/−)-9-(2,3-Dimethoxy-benzoylamino)-4-oxo-2-pyrimidin-4-yl-5,6,8,9-tetrahydro-4H-1,4a,7-triaza-benzocycloheptene-7-carboxylic acid ethyl ester
18. (+/−)-9-(2-Methoxy-4-trifluoromethyl-benzoylamino)-4-oxo-2-pyrimidin-4-yl-5,6,8,9-tetrahydro-4H-1,4a,7-triaza-benzocycloheptene-7-carboxylic acid ethyl ester
19. (+/−)-9-(4-Bromo-benzoylamino)-4-oxo-2-pyrimidin-4-yl-5,6,8,9-tetrahydro-4H-1,4a,7-triaza-benzocycloheptene-7-carboxylic acid ethyl ester
20. (+/−)-9-(4-Fluoro-2-trifluoromethyl-benzoylamino)-4-oxo-2-pyrimidin-4-yl-5,6,8,9-tetrahydro-4H-1,4a,7-triaza-benzocycloheptene-7-carboxylic acid ethyl ester
21. (+/−)-9-(2-Methoxy-benzoylamino)-4-oxo-2-pyrimidin-4-yl-5,6,8,9-tetrahydro-4H-1,4a,7-triaza-benzocycloheptene-7-carboxylic acid ethyl ester
22. (+/−)-2-Methoxy-N-(4-oxo-2-pyrimidin-4-yl-4,5,6,7,8,9-hexahydro-1,4a,7-triaza-benzocyclohepten-9-yl)-benzamide
23. (+/−)-5-Bromo-2-methoxy-N-(4-oxo-2-pyrimidin-4-yl-4,5,6,7,8,9-hexahydro-1,4a,7-triaza-benzocyclohepten-9-yl)-benzamide
24. (+/−)-2,3-Dimethoxy-N-(4-oxo-2-pyrimidin-4-yl-4,5,6,7,8,9-hexahydro-1,4a,7-triaza-benzocyclohepten-9-yl)-benzamide
25. (+/−)-9-Benzylamino-4-oxo-2-pyrimidin-4-yl-5,6,8,9-tetrahydro-4H-1,4a,7-triaza-benzocycloheptene-7-carboxylic acid ethyl ester
26. (+/−)-2,3-Dimethoxy-N-(7-methyl-4-oxo-2-pyrimidin-4-yl-4,5,6,7,8,9-hexahydro-1,4a,7-triaza-benzocyclohepten-9-yl)-benzamide
27. (+/−)-9-Benzylamino-2-pyrimidin-4-yl-6,7,8,9-tetrahydro-5H-1,4a,7-triaza-benzocyclohepten-4-one
28. (+/−)-9-[4-(1-Methyl-1H-pyrazol-4-yl)-benzoylamino]-4-oxo-2-pyrimidin-4-yl-5,6,8,9-tetrahydro-4H-1,4a,7-triaza-benzocycloheptene-7-carboxylic acid ethyl ester
29. (+/−)-4-Amino-5-chloro-2-methoxy-N-(4-oxo-2-pyrimidin-4-yl-4,5,6,7,8,9-hexahydro-1,4a,7-triaza-benzocyclohepten-9-yl)-benzamide
30. (+/−)-5-Bromo-2-methoxy-N-(7-methyl-4-oxo-2-pyrimidin-4-yl-4,5,6,7,8,9-hexahydro-1,4a,7-triaza-benzocyclohepten-9-yl)-benzamide
31. (+/−)-5-Chloro-2-methoxy-N-(7-methyl-4-oxo-2-pyrimidin-4-yl-4,5,6,7,8,9-hexahydro-1,4a,7-triaza-benzocyclohepten-9-yl)-benzamide
32. (+/−)-5-Chloro-2-methoxy-N-(4-oxo-2-pyrimidin-4-yl-4,5,6,7,8,9-hexahydro-1,4a,7-triaza-benzocyclohepten-9-yl)-benzamide
33. (+/−)-9-(2,4-Dimethoxy-benzoylamino)-4-oxo-2-pyridin-4-yl-5,6,8,9-tetrahydro-4H-1,4a,7-triaza-benzocycloheptene-7-carboxylic acid ethyl ester
34. (+/−)-9-(5-Chloro-2-methoxy-benzoylamino)-4-oxo-2-pyridin-4-yl-5,6,8,9-tetrahydro-4H-1,4a,7-triaza-benzocycloheptene-7-carboxylic acid ethyl ester
35. (+/−)-9-(4-Fluoro-2-methoxy-benzoylamino)-4-oxo-2-pyridin-4-yl-5,6,8,9-tetrahydro-4H-1,4a,7-triaza-benzocycloheptene-7-carboxylic acid ethyl ester
36. (+/−)-9-[(4-Chloro-2-methoxy-benzoyl)-methyl-amino]-4-oxo-2-pyridin-4-yl-5,6,8,9-tetrahydro-4H-1,4a,7-triaza-benzocycloheptene-7-carboxylic acid ethyl ester
37. (+/−)-2-Methoxy-4-(5-methyl-[1,2,4]oxadiazol-3-yl)-N-(4-oxo-2-pyrimidin-4-yl-4,5,6,7,8,9-hexahydro-1,4a,7-triaza-benzocyclohepten-9-yl)-benzamide 38. (+/−)-2-Methoxy-4-(5-methyl-[1,2,4]oxadiazol-3-yl)-N-(7-methyl-4-oxo-2-pyrimidin-4-yl-4,5,6,7,8,9-hexahydro-1,4a,7-triaza-benzocyclohepten-9-yl)-benzamide
39. (+/−)-4-Fluoro-2-methoxy-N-(7-methyl-4-oxo-2-pyridin-4-yl-4,5,6,7,8,9-hexahydro-1,4a,7-triaza-benzocyclohepten-9-yl)-benzamide
40. (+/−)-N-(7-Isopropyl-4-oxo-2-pyridin-4-yl-4,5,6,7,8,9-hexahydro-1,4a,7-triaza-benzocyclohepten-9-yl)-2-methoxy-benzamide
41. (+/−)-2-Methoxy-N-(4-oxo-2-pyridin-4-yl-4,5,6,7,8,9-hexahydro-1,4a,7-triaza-benzocyclohepten-9-yl)-benzamide
42. (+/−)-4-Chloro-N-(7-cyclopropylmethyl-4-oxo-2-pyridin-4-yl-4,5,6,7,8,9-hexahydro-1,4a,7-triaza-benzocyclohepten-9-yl)-2-methoxy-benzamide
43. (+/−)-2-Methoxy-N-(4-oxo-2-pyridin-4-yl-4,5,6,7,8,9-hexahydro-1,4a,7-triaza-benzocyclohepten-9-yl)-4-trifluoromethyl-benzamide
44. (+/−)-N-(7-Isopropyl-4-oxo-2-pyridin-4-yl-4,5,6,7,8,9-hexahydro-1,4a,7-triaza-benzocyclohepten-9-yl)-2-methoxy-4-trifluoromethyl-benzamide
45. (+/−)-N-(7-Cyclopropylmethyl-4-oxo-2-pyridin-4-yl-4,5,6,7,8,9-hexahydro-1,4a,7-triaza-benzocyclohepten-9-yl)-2,5-dimethoxy-benzamide
46. (+/−)-2,5-Dimethoxy-N-(4-oxo-2-pyridin-4-yl-4,5,6,7,8,9-hexahydro-1,4a,7-triaza-benzocyclohepten-9-yl)-benzamide
47. (+/−)-4-Fluoro-N-(4-oxo-2-pyridin-4-yl-4,5,6,7,8,9-hexahydro-1,4a,7-triaza-benzocyclohepten-9-yl)-2-trifluoromethyl-benzamide
48. (+/−)-5-Chloro-2-methoxy-N-(4-oxo-2-pyridin-4-yl-4,5,6,7,8,9-hexahydro-1,4a,7-triaza-benzocyclohepten-9-yl)-benzamide
49. (+/−)-4-Fluoro-N-(7-methyl-4-oxo-2-pyridin-4-yl-4,5,6,7,8,9-hexahydro-1,4a,7-triaza-benzocyclohepten-9-yl)-2-trifluoromethyl-benzamide
50. (+/−)-N-(7-Benzyl-4-oxo-2-pyridin-4-yl-4,5,6,7,8,9-hexahydro-1,4a,7-triaza-benzocyclohepten-9-yl)-5-chloro-2-methoxy-benzamide As a further object, the present invention concerns also methods for preparing the pyrimidone compounds represented by the aforementioned formula (I).

These compounds can be prepared, for example, according to methods explained below.

Preparation Method

Pyrimidone compounds represented by the aforementioned formula (I), may be prepared according to the method described in the scheme 1.

Scheme 1

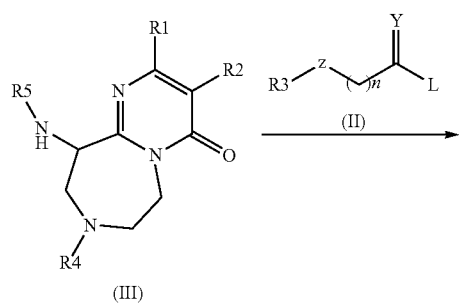

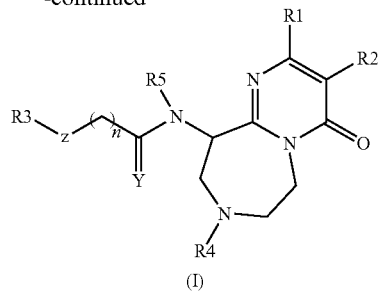

(In the above scheme the definition of R1, R2, R3, R4, R5, n, Y and Z are the same as those already described for compound of formula (I)).

Following this method, the pyrimidone derivative represented by the above formula (III), wherein R1, R2, R4 and R5, are as defined for compound of formula (I) are used as intermediates. Alternatively compounds of formula (III) are allowed to react with a base such as triethylamine, sodium carbonate or potassium carbonate in a solvent such as tetrahydrofuran, N-methylpyrrolidone, N,N-dimethylacetamide or chloroform at a suitable temperature ranging from 0 to 130° C. under ordinary air, then with a compound of formula (II), wherein R3, Z, Y and n are as defined for compound of formula (I) and L represents a leaving group preferably chlorine, bromide or mesyl group, to obtain the compound of the aforementioned formula (I).

Alternatively compounds of formula (I) wherein Y represents two hydrogen atoms may be prepared by reductive amination of a compound of formula (II) wherein Y represents an oxygen atom and L represents a hydrogen atom, by a compound of formula (III) wherein R1, R2, R4 and R5 are as defined for compound of formula (I), according to well known methods to one skilled in the art.

Compound of formula (II) is commercially available or may be synthesized according to well-known methods to one skilled in the art.

Compound of formula (III) may be prepared according to the method defined in scheme 2.

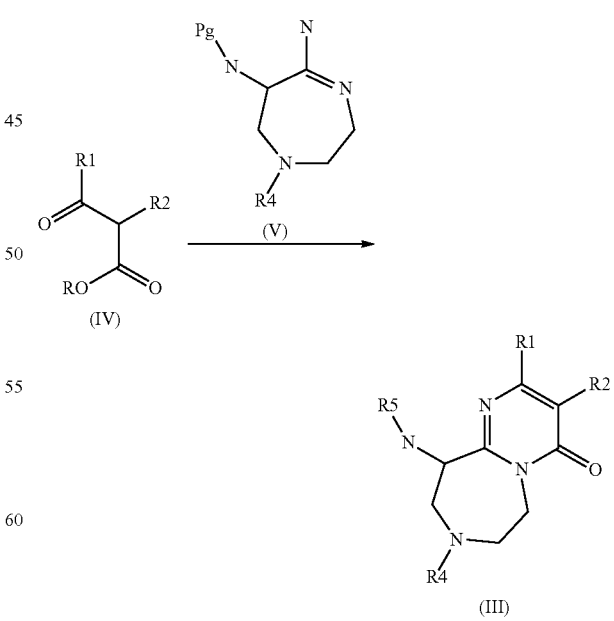

Scheme 2

As a further object, the present invention concerns also intermediate (V) for preparing the pyrimidone compounds represented by the aforementioned formula (I).

(In the above scheme the definitions of Pg, R1, R2 and R4 are the same as already described and Pg represents a benzyl group, a tert-butoxy carbonyl group, an ethoxy carbonyl group, an acetyl group, a phthalimido group, a benzyloxy carbonyl.

According to this method, the 3-ketoester of formula (IV), wherein R1 and R2 are as defined for compound of formula (I), R is an alkyl group such as for example methyl or ethyl, is allowed to react with a compound of formula (V) wherein R4 is as defined for compound of formula (I) and Pg is a suitable protecting group such as for example a phthalimido group. The reaction may be carried out in the presence of a base such as potassium carbonate, in an alcoholic solvent such as methanol, ethanol and the like or without, at a suitable temperature ranging from 25° to 140° C. under ordinary air to obtain the compound of the aforementioned formula (III).

Additionally compound of formula (III) wherein R2 represents a hydrogen atom may be halogenated in order to give compounds of formula (III) wherein R2 is a halogen atom such as a bromine atom or a chlorine atom. The reaction may be carried out in an acidic medium such as acetic acid or propionic acid, in presence of bromosuccinimide, chlorosuccinimide or bromine.

In addition, compounds of formula (IV) wherein R2 represents a fluorine atom may be obtained by analogy to the method described in Tetrahedron Letters, Vol. 30, No. 45, pp 6113-6116, 1989.

In addition, compounds of formula (IV) wherein R2 represents a hydrogen atom may be obtained by analogy to the method described in patent DE 2705582.

As a further object, the present invention concerns also the compounds of formula (III) as intermediates of compounds of formula (I).

Compound of formula (IV) is commercially available or may be synthesized according to well-known methods to one skilled in the art.

For example compounds of formula (IV), wherein R1 represents a pyridine ring or a pyrimidine ring, optionally substituted by a $C_{1-6}$ alkyl group, $C_{1-6}$ alkoxy group or a halogen atom, can be prepared by reacting respectively an isonicotinic acid or a pyrimidine-carboxylic acid, optionally substituted by a $C_{1-6}$ alkyl group, $C_{1-6}$ alkoxy group or a halogen, with the corresponding malonic acid monoester. The reaction can be carried out using methods well known to one skilled in the art, such as for example in presence of a coupling agent such as 1,1'-carbonylbis-1H-imidazole in a solvent such as tetrahydrofuran at a temperature ranging from 20 to 70° C.

For example compound of formula (V), wherein R4 is as defined for compound of formula (I) and a suitable protecting group Pg such as for example a phthalimido group, may be prepared according to the method defined in scheme 3, starting from compound of formula (VI). The conditions which may be used are given in the chemical examples.

Scheme 3

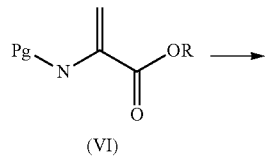

(VI)

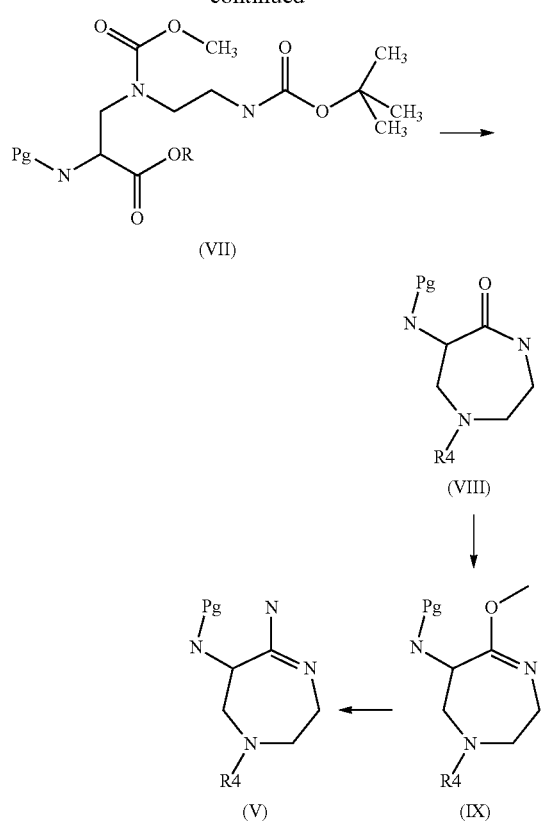

Compound of formula (VI) may be synthesized according to the method described in Synthetic Communications, 33(8), 1375-1382; 2003.

Compound of formula (VII) may be synthesized by addition of a suitable nucleophile on compound of formula (VI).

Compound of formula (VII) may cyclise to obtain the compound of the aforementioned formula (VIII).

Compounds of formula (IX) and formula (V) may be synthesized according to the method described in WO96/14844 from compound of formula (VIII).

Alternatively compounds of formula (III) wherein R1, R2 and R4 are as defined for compound of formula (I), may be prepared according to the method defined in scheme 4, starting from compound of formula (IV). The conditions which may be used are given in the chemical examples.

Scheme 4

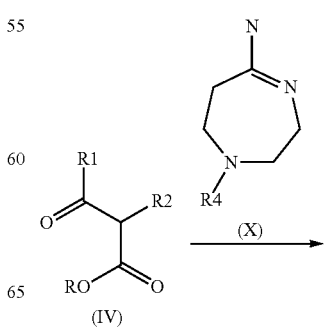

(IV)

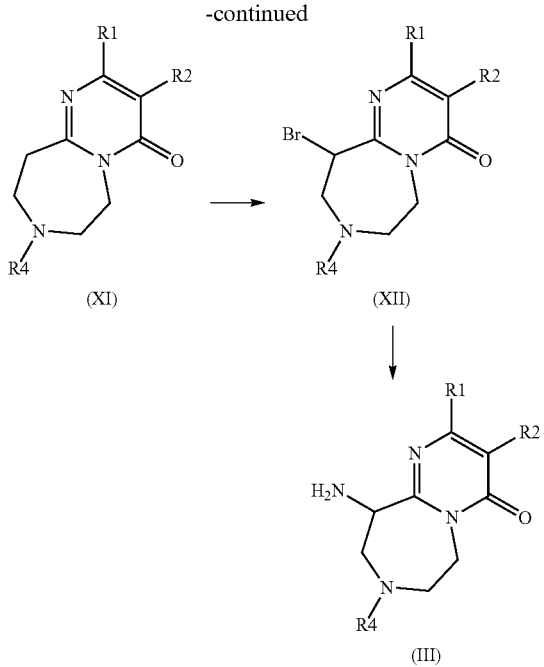

As a further object, the present invention concerns also intermediates (III), (XI) and (XII) for preparing the pyrimidone compounds represented by the aforementioned formula (I).

According to this method, the 3-ketoester of formula (IV), wherein R1, R2 and R4 are as defined for compound of formula (I), R is an alkyl group such as for example methyl or ethyl, is allowed to react with a compound of formula (X) wherein R4 is as defined for compound of formula (I). The reaction may be carried out in the presence of a base such as potassium carbonate, in an alcoholic solvent such as methanol, ethanol and the like or without, at a suitable temperature ranging from 25° to 140° C. under ordinary air to obtain the compound of the aforementioned formula (XI).

The compound of formula (XI) wherein R1, R2 and R4 are as defined for compound of formula (I) can be deprotonated with strong base (such as lithium bis(trimethylsilyl)amide or lithium diisopropyl amide) and the resultant anion reacted with bromine or N-bromosuccinimide to afford the compound of formula (XII).

The compound of formula (XII) wherein R1, R2 and R4 are as defined for compound of formula (I) can react with suitable nucleophilic nitrogen sources such as ammonia, 4-methoxybenzylamine to afford the compound of formula (III).

Compound of formula (X) may be synthesized according to the method described in WO97/16430 and Tetrahedron Letters, Vol. 32, No. 22, pp 2469-2470, 1991.

In the above reactions protection or deprotection of a functional group may sometimes be necessary. A suitable protecting group Pg can be chosen depending on the type of the functional group, and a method described in the literature may be applied. Examples of protecting groups, of protection and deprotection methods are given for example in Greene's Protective groups in Organic Synthesis, Greene et al., 4$^{th}$ Ed. 2007 (John Wiley & Sons, Inc., New York).

The compounds of the present invention have inhibitory activity against GSK3β. Accordingly, the compounds of the present invention are useful as an active ingredient for the preparation of a medicament, which enables preventive and/or therapeutic treatment of a disease caused by abnormal GSK3β activity and more particularly of neurodegenerative diseases such as Alzheimer's disease. In addition, the compounds of the present invention are also useful as an active ingredient for the preparation of a medicament for preventive and/or therapeutic treatment of neurodegenerative diseases such as Parkinson's disease, tauopathies (e.g. Fronto temporal dementia, corticobasal degeneration, Pick's disease, progressive supranuclear palsy), Wilson's disease, Huntington's disease, Prion disease and other dementia including vascular dementia; acute stroke and others traumatic injuries; cerebrovascular accidents (e.g. age related macular degeneration); brain and spinal cord trauma; amyotrophic lateral sclerosis, peripheral neuropathies; retinopathies and glaucoma; and other diseases such as non-insulin dependent diabetes (such as diabetes type II) and obesity; malaria, manic depressive illness; schizophrenia; alopecia; cancers such as colorectal, prostate breast cancer, non-small cell lung carcinoma, thyroid cancer, T or B-cell leukemia, several virus-induced tumours and in bone related pathologies; parenchymal renal diseases or muscle atrophy. The medicament could also find an application in regenerative medicine. The medicament could also find an application in the treatment or prevention of Pemphigus vulgaris. The medicament could also find an application in the treatment of neutropenia induced by cancer chemotherapy. The medicament could also find an application for therapeutic treatment of a disease characterized by cognitive and memory deficits such as in Alzheimer's disease, Parkinson disease, age-associated memory impairment, mild cognitive impairment, brain trauma, schizophrenia and other conditions in which such deficits are observed.

The present invention further relates to a method for treating neurodegenerative diseases caused by abnormal activity of GSK3β and of the aforementioned diseases which comprises administering to a mammalian organism in need thereof an effective amount of a compound of the formula (I).

As the active ingredient of the medicament of the present invention, a substance may be used which is selected from the group consisting of the compound represented by the aforementioned formula (I) and pharmacologically acceptable salts thereof, and solvates thereof and hydrates thereof. The substance, per se, may be administered as the medicament of the present invention, however, it is desirable to administer the medicament in a form of a pharmaceutical composition which comprises the aforementioned substance as an active ingredient and one or more pharmaceutical additives. As the active ingredient of the medicament of the present invention, two or more of the aforementioned substances may be used in combination. The above pharmaceutical composition may be supplemented with an active ingredient of another medicament for the treatment of the above mentioned diseases. The type of pharmaceutical composition is not particularly limited, and the composition may be provided as any formulation for oral or parenteral administration. For example, the pharmaceutical composition may be formulated, for example, in the form of pharmaceutical compositions for oral administration such as granules, fine granules, powders, hard capsules, soft capsules, syrups, emulsions, suspensions, solutions and the like, or in the form of pharmaceutical compositions for parenteral administrations such as injections for intravenous, intramuscular, or subcutaneous administration, drip infusions, transdermal preparations, transmucosal preparations, nasal drops, inhalants, suppositories and the like. Injections or drip infusions may be prepared as powdery preparations such as in the form of lyophilized preparations, and may be used by dissolving just before use in an appropriate aqueous medium such as physiological saline. Sustained-release preparations such as those coated with a polymer may be directly administered intracerebrally.

Types of pharmaceutical additives used for the manufacture of the pharmaceutical composition, content ratios of the pharmaceutical additives relative to the active ingredient, and methods for preparing the pharmaceutical composition may be appropriately chosen by those skilled in the art. Inorganic or organic substances, or solid or liquid substances may be used as pharmaceutical additives. Generally, the pharmaceutical additives may be incorporated in a ratio ranging from 1% by weight to 90% by weight based on the weight of an active ingredient.

Examples of excipients used for the preparation of solid pharmaceutical compositions include, for example, lactose, sucrose, starch, talc, cellulose, dextrin, kaolin, calcium carbonate and the like. For the preparation of liquid compositions for oral administration, a conventional inert diluent such as water or a vegetable oil may be used. The liquid composition may contain, in addition to the inert diluent, auxiliaries such as moistening agents, suspension aids, sweeteners, aromatics, colorants, and preservatives. The liquid composition may be filled in capsules made of an absorbable material such as gelatin. Examples of solvents or suspension mediums used for the preparation of compositions for parenteral administration, e.g. injections, suppositories, include water, propylene glycol, polyethylene glycol, benzyl alcohol, ethyl oleate, lecithin and the like. Examples of base materials used for suppositories include, for example, cacao butter, emulsified cacao butter, lauric lipid, witepsol.

The dose and frequency of administration of the medicament of the present invention are not particularly limited, and they may be appropriately chosen depending on conditions such as a purpose of preventive and/or therapeutic treatment, a type of a disease, the body weight or age of a patient, severity of a disease and the like. Generally, a daily dose for oral administration to an adult may be 0.01 to 1,000 mg (the weight of an active ingredient), and the dose may be administered once a day or several times a day as divided portions, or once in several days. When the medicament is used as an injection, administrations may preferably be performed continuously or intermittently in a daily dose of 0.001 to 100 mg (the weight of an active ingredient) to an adult.

CHEMICAL EXAMPLES

Example 1

Compound No. 1 of Table 1

(+/−)-9-(4-Chloro-2-methoxy-benzoylamino)-4-oxo-2-pyrimidin-4-yl-5,6,8,9-tetrahydro-4H-1,4a,7-triaza-benzocycloheptene-7-carboxylic acid ethyl ester 1.1 (+/−)-3-(2-tert-Butoxycarbonylamino-ethylamino)-2-(1,3-dioxo-1,3-dihydro-isoindol-2-yl)-propionic acid methyl ester To a solution of 12.60 g (51.38 mmol) of 2-(1,3-dioxo-1,3-dihydro-isoindol-2-yl)-acrylic acid methyl ester (described in Synthetic Communications, 33(8), 1375-1382; 2003) dissolved in 170 mL of acetonitrile was added at room temperature 42.60 g (308.28 mmol) of potassium carbonate and 9.05 g (56.52 mmol) of (2-amino-ethyl)-carbamic acid tert-butyl ester. The resulting mixture was stirred at room temperature for 12 h. 300 mL of dichloromethane was added and the mixture was filtered and the solid obtained was triturated with dichloromethane, filtered, and the resulting filtrates were evaporated to dryness. The residue was dissolved in diethyl ether, washed with a saturated aqueous solution of sodium hydrogen carbonate, saturated aqueous solution of sodium chloride, dried over sodium sulfate and evaporated to dryness. The residue was chromatographed on silica gel eluting with a mixture of chloroform/methanol/aqueous ammonia solution (29%) in the proportions 98/2/0.2 led to afford 6.50 g (31%) of the desired compound.

NMR $^1$H(CDCl$_3$; 200 MHz)

δ (ppm): 7.80 (m, 2H), 7.65 (m, 2H), 4.88 (m, 1H), 4.80 (sl, 1H), 4.12 (m, 2H), 3.28 (m, 2H), 3.07 (m, 2H), 2.64 (m, 2H), 1.30 (s, 9H), 1.12 (t, 3H)

1.2 (+/−)-3-[(2-tert-Butoxycarbonylamino-ethyl)-ethoxycarbonyl-amino]-2-(1,3-dioxo-1,3-dihydro-isoindol-2-yl)-propionic acid methyl ester To a solution of 18.80 g (47.54 mmol) of 3-(2-tert-butoxycarbonylamino-ethylamino)-2-(1,3-dioxo-1,3-dihydro-isoindol-2-yl)-propionic acid methyl ester dissolved in 156 mL of anhydrous dichloromethane was added 8.02 mL (57.05 mmol) of triethylamine. The resulting mixture was cooled at 0° C. and 5.00 mL (52.29 mmol) of ethyl chloroformate dissolved in 30 mL of anhydrous dichloromethane was added. The resulting mixture was stirred at room temperature for 12 h. Saturated aqueous solution of ammonium chloride was added and the mixture extracted with dichloromethane. The extracts were washed with a saturated aqueous solution of sodium chloride, sodium carbonate, dried over sodium sulfate and evaporated to dryness. The residue was chromatographed on silica gel eluting with a mixture of dichloromethane/methanol in the proportions 99/1 led to afford 20.00 g (90%) of the desired compound as an oil.

NMR $^1$H (DMSO; 400 MHz)

δ (ppm): 7.91 (m, 4H), 6.81 (sl, 1H), 5.22 (m, 1H), 4.07 (m, 1H), 3.80 (m, 2H), 3.70 (s, 3H), 3.47 (m, 1H), 3.20 (m, 2H), 3.08 (m, 2H), 1.38 (s, 9H), 0.90 (m, 3H).

1.3 (+/−)-N-{2-[(2-Amino-ethyl)-ethoxycarbonyl-amino]-1-carboxy-ethyl}-phthalamic acid To a solution of 218.80 g (470.35 mmol) of 3-[(2-tert-butoxycarbonylamino-ethyl)-ethoxycarbonyl-amino]-2-(1, 3-dioxo-1,3-dihydro-isoindol-2-yl)-propionic acid methyl ester dissolved in 600 mL of tetrahydrofuran was added 100 mL of water and 39.47 g (940.70 mmol) of lithium hydroxide monohydrate. The resulting mixture was heated at 65° C. for 2 h. 19.73 g (470.35 mmol) of lithium hydroxide monohydrate was added. The resulting mixture was stirred at 65° C. for 1 h. The mixture was evaporated to dryness. Toluene was added to the residue and evaporated to dryness to give 225.00 g of the desired compound as a lithium salt. To the resulting lithium salt (225.00 g) suspension in 1 L of dichloromethane was added slowly 500 mL of trifluoroacetic acid. The resulting mixture was stirred at room temperature for 2 h30 and evaporated to dryness. The residue was triturated with a mixture of diethyl ether/dichloromethane and filtered to afford 300.00 g (89%) of a powder. The compound was used as such in the next step.

1.4 (+/−)-6-(1,3-Dioxo-1,3-dihydro-isoindol-2-yl)-5-oxo-[1,4]diazepane-1-carboxylic acid ethyl ester To a solution of 150.00 g (208.00 mmol) of N-{2-[(2-amino-ethyl)-ethoxycarbonyl-amino]-1-carboxy-ethyl}-phthalamic acid dissolved in 3 L of anhydrous dimethylformamide was added 75.50 mL (686.40 mmol) of N-methylmorpholine. The resulting mixture was stirred at room temperature for 10 min and 143.00 g (520.00 mmol) of diphenylphosphoryl azide was added. The mixture was stirred at room temperature for 36 h and evaporated to dryness. The mixture was dissolved in dichloromethane, washed with a saturated aqueous solution of ammonium chloride, saturated aqueous solution of sodium hydrogen carbonate, dried over sodium sulfate and evaporated to dryness. The residue was chromatographed on silica gel eluting with a mixture of dichloromethane/methanol/aqueous ammonia solution (29%) in the proportions 96/4/0.6 led to afford 23.00 g (33%) of the desired compound.

Mp: 195-197° C.

NMR $^1$H (DMSO; 400 MHz)

δ (ppm): 8.19 (m, 1H), 7.92 (m, 4H), 4.80 (m, 1H), 4.22-4.03 (m, 4H), 3.88 (m, 1H), 3.42 (m, 1H), 3.28 (m, 1H), 3.08 (m, 1H), 1.22 (m, 3H).

1.5 (+/−)-6-(1,3-Dioxo-1,3-dihydro-isoindol-2-yl)-5-methoxy-2,3,6,7-tetrahydro-[1,4]diazepine-1-carboxylic acid ethyl ester To a solution of 45.00 g (135.82 mmol) of (+/−)-6-(1,3-dioxo-1,3-dihydro-isoindol-2-yl)-5-oxo-[1,4]diazepane-1-carboxylic acid ethyl ester in 339 mL of anhydrous dichloromethane was added 22.09 g (149.40 mmol) of trimethyloxonium tetrafluoroborate. The resulting mixture was stirred at room temperature for 12 h. The mixture was hydrolyzed with a saturated aqueous solution of sodium hydrogen carbonate, extracted with dichloromethane, dried over sodium sulfate and the solvent was evaporated to afford 46.90 g (99%) of pure product as yellow oil. The compound was used as such in the next step.

NMR $^1$H (CDCl$_3$; 200 MHz)

δ (ppm): 7.90 (m, 2H), 7.80 (m, 2H), 4.95 (m, 1H), 4.15-3.85 (m, 6H), 3.60 (m, 1H), 3.48 (m, 3H), 3.20 (m, 1H), 1.12 (m, 3H).

1.6 (+/−)-9-(1,3-Dioxo-1,3-dihydro-isoindol-2-yl)-4-oxo-2-pyrimidin-4-yl-5,6,8,9-tetrahydro-4H-1,4a,7-triaza-benzocycloheptene-7-carboxylic acid ethyl ester To a solution of 39.00 g (112.93 mmol) of (+/−)-6-(1,3-dioxo-1,3-dihydro-isoindol-2-yl)-5-methoxy-2,3,6,7-tetrahydro-[1,4]diazepine-1-carboxylic acid ethyl ester dissolved in 350 mL of methanol was added 6.34 g (118.57 mmol) of ammonium chloride at room temperature. The resulting mixture was stirred under reflux for 12 h. The cooled solution was evaporated to remove solvent. The residue was triturated with diethyl ether and filtered to afford 33.00 g (80%) of (+/−)-5-Amino-6-(1,3-dioxo-1,3-dihydro-isoindol-2-yl)-2,3,6,7-tetrahydro-[1,4]diazepine-1-carboxylic acid ethyl ester hydrochloride (1:1) as a white powder. The compound was used as such in the next step.

To a suspension of 33.00 g (89.97 mmol) of (+/−)-5-amino-6-(1,3-dioxo-1,3-dihydro-isoindol-2-yl)-2,3,6,7-tetrahydro-[1,4]diazepine-1-carboxylic acid ethyl ester hydrochloride (1:1) in 300 mL of tetrahydrofuran was added 6.47 g (161.94 mmol) of sodium hydride (60% in oil), the reaction mixture was stirred at room temperature for 1 h and 17.47 g (89.97 mmol) of ethyl 3-(pyrimidin-4-yl)-3-oxopropionate dissolved in 300 mL of toluene was added. The resulting solution was evaporated to remove tetrahydrofuran, heated under reflux and 5.00 mL of glacial acetic acid was added. The reaction mixture was stirred under reflux for 12 h. The cooled solution was evaporated to remove solvent. The mixture was dissolved in dichloromethane, washed with a saturated aqueous solution of ammonium chloride, saturated aqueous sodium chloride, dried over sodium sulfate and evaporated to dryness. The residue was triturated with diethyl ether and filtered to afford 18.60 g (45%) of the product as a brown powder. The compound was used as such in the next step.

NMR $^1$H (DMSO; 300 MHz)

δ (ppm): 9.28 (s, 1H), 8.68 (d, 1H), 8.01 (m, 4H), 7.24 (m, 2H), 5.71 (m, 1H), 5.18 (m, 1H), 4.51 (m, 1H), 4.30 (m, 1H), 4.12 (m, 5H), 1.22 (m, 3H)

1.7 (+/−)-9-Amino-4-oxo-2-pyrimidin-4-yl-5,6,8,9-tetrahydro-4H-1,4a,7-triaza-benzocycloheptene-7-carboxylic acid ethyl ester hydrobromide (1:1)

To a solution of 18.60 g (40.40 mmol) of (+/−)-9-(1,3-dioxo-1,3-dihydro-isoindol-2-yl)-4-oxo-2-pyrimidin-4-yl-5,6,8,9-tetrahydro-4H-1,4a,7-triaza-benzocycloheptene-7-carboxylic acid ethyl ester dissolved in 200 mL of ethanol was added 19.60 mL (403.95 mmol) of hydrazine hydrate and the resulting mixture was stirred under reflux for 2 hours. The mixture was filtered and the solid obtained was triturated with dichloromethane, filtered, the resulting filtrates were washed with a saturated aqueous solution of sodium carbonate, saturated aqueous sodium chloride, dried over sodium sulfate and evaporated to dryness. The residue was converted to the hydrobromide salt by addition of hydrobromic acid (33 wt % solution in glacial acetic acid) to an isopropylic solution of the free base. 9.70 g (72%) of a brown solid is obtained.

Mp: 243-246° C.

NMR $^1$H (DMSO; 400 MHz)

δ (ppm): 9.32 (s, 1H), 9.05 (d, 1H), 8.44 (d, 1H), 7.28 (s, 1H), 4.89 (m, 1H), 4.40 (m, 1H), 4.12-4.01 (m, 3H), 3.90 (m, 1H), 3.75 (m, 1H), 3.50 (m, 2H), 2.32 (br s, 2H), 1.15 (t, 3H)

1.8 (+/−)-9-(4-Chloro-2-methoxy-benzoylamino)-4-oxo-2-pyrimidin-4-yl-5,6,8,9-tetrahydro-4H-1,4a,7-triaza-benzocycloheptene-7-carboxylic acid ethyl ester To a solution of 0.060 g (0.18 mmol) of (+/−)-9-amino-4-oxo-2-pyrimidin-4-yl-5,6,8,9-tetrahydro-4H-1,4a,7-triaza-benzocycloheptene-7-carboxylic acid ethyl ester hydrobromide (1:1) dissolved in 1.80 mL of dimethylformamide was added 0.037 g (0.20 mmol) of 4-chloro-2-methoxy-benzoic acid. To the resulting mixture was added 40 µL (0.22 mmol) of diethyl cyanophosphonate and 30 µl (0.20 mmol) of triethylamine at 0° C. The resulting mixture was stirred at room temperature for 2 hours and evaporated to dryness. Water was added and the mixture extracted with dichloromethane. The extracts were washed with a saturated aqueous solution of sodium carbonate, saturated aqueous solution of ammonium chloride, saturated aqueous sodium chloride dried and evaporated. The residue was triturated with a mixture of diethyl ether/ethyl acetate and filtered to afford 0.048 g (53%) of the pure product as a powder.

Mp: 175-177° C.

NMR $^1$H (DMSO; 400 MHz)

δ (ppm): 9.40 (s, 1H), 9.28 (m, 1H), 9.10 (d, 1H), 8.28 (m, 1H), 7.98 (d, 1H), 7.38 (s, 1H), 7.35 (s, 1H), 7.21 (d, 1H), 5.59 (m, 1H), 5.01 (m, 1H), 4.24 (m, 1H), 4.05 (s, 3H), 4.02 (m, 4H), 3.58 (m, 1H), 3.41 (m, 1H), 1.18 (t, 3H).

Example 2

Compound No. 2 of Table 1

(+/−)-4-Chloro-2-methoxy-N-(4-oxo-2-pyrimidin-4-yl-4,5,6,7,8,9-hexahydro-1,4a,7-triaza-benzocyclohepten-9-yl)-benzamide hydrochloride (1:1)

2.1 (+/−)-9-Amino-2-pyrimidin-4-yl-6,7,8,9-tetrahydro-5H-1,4a,7-triaza-benzocyclohepten-4-one dihydrobromide (2:1)

To a solution of 9.70 g (23.59 mmol) of (+/−)-9-amino-4-oxo-2-pyrimidin-4-yl-5,6,8,9-tetrahydro-4H-1,4a,7-triaza-benzocycloheptene-7-carboxylic acid ethyl ester dissolved in 118 mL of glacial acetic acid was added 41.38 mL (235.86 mmol) of hydrobromic acid (33 wt % solution in glacial acetic acid). The resulting mixture was stirred at 90° C. for 16 hours, cooled and evaporated to dryness. Toluene was added to the residue and evaporated. Ethanol was added to the residue and evaporated. The crude was triturated with diethyl ether and filtered to afford 12.40 g of the product as a brown powder.

Mp: 225-235° C.

NMR $^1$H (DMSO; 400 MHz)

δ (ppm): 9.40 (s, 1H), 9.20 (d, 1H), 9.06 (br s, 2H), 8.61 (m, 1H), 7.40 (s, 1H), 5.28 (m, 2H), 4.55-4.18 (m, 2H), 4.03 (m, 1H), 3.82-3.52 (m, 2H), 3.32 (m, 1H).

2.2 (+/−)-4-Chloro-2-methoxy-N-(4-oxo-2-pyrimidin-4-yl-4,5,6,7,8,9-hexahydro-1,4a,7-triaza-benzocyclohepten-9-yl)-benzamide hydrochloride (1:1)

To a solution of 0.163 g (0.88 mmol) of 4-chloro-2-methoxy-benzoic acid dissolved in 20 mL of anhydrous dichloromethane was added 0.27 mL (1.97 mmol) of triethylamine, 0.168 g (0.88 mmol) of 1-(3-dimethylaminopropyl)-3-ethylcarbodiimide hydrochloride and 0.118 g (0.88 mmol) of 1-hydroxybenzotriazole. The resulting mixture was stirred at room temperature for 10 min and added slowly at −10° C. to a solution of 0.460 g (1.09 mmol) of (+/−)-9-amino-2-pyrimidin-4-yl-6,7,8,9-tetrahydro-5H-1,4a,7-triaza-benzocyclohepten-4-one dihydrobromide (2:1) dissolved in a mixture of 100 mL of anhydrous dichloromethane and 0.40 mL (2.85 mmol) of triethylamine. The resulting mixture was stirred at −10° C. for 3 hours and at room temperature for 16 hours. The reaction mixture was washed with a saturated aqueous solution of sodium carbonate, saturated aqueous sodium chloride, dried over sodium sulfate and evaporated to dryness. The residue was chromatographed on silica gel eluting with a mixture of dichloromethane/methanol/aqueous ammonia solution (29%) in the proportions 97/3/0.3 to afford 0.240 g (51%) of the pure product as a powder. 0.200 g of the pure product was converted to the hydrochloride salt by addition of hydrochloric acid (5-6N in isopropanol) to an isopropylic solution of the free base. There is obtained 0.180 g (83%) of product as a white solid.

Mp: 256-258° C.

NMR $^1$H (DMSO; 400 MHz)

δ (ppm): 9.41 (m, 2H), 9.18 (d, 1H), 8.28 (m, 1H), 8.00 (d, 1H), 7.40 (m, 2H), 7.22 (d, 1H), 5.78 (m, 1H), 5.25 (m, 1H), 4.10 (m, 1H), 4.02 (s, 3H), 3.61 (m, 2H), 3.41 (m, 1H), 3.18 (m, 1H).

Example 3

Compound No. 3 of Table 1

(+/−)-4-Chloro-2-methoxy-N-(7-methyl-4-oxo-2-pyrimidin-4-yl-4,5,6,7,8,9-hexahydro-1,4a,7-triaza-benzocyclohepten-9-yl)-benzamide hydrochloride (1:1)

To a solution of 0.040 g (0.09 mmol) of (+/−)-4-chloro-2-methoxy-N-(4-oxo-2-pyrimidin-4-yl-4,5,6,7,8,9-hexahydro-1,4a,7-triaza-benzocyclohepten-9-yl)-benzamide in 1.9 ml of methanol was added 0.003 g (0.04 mmol) of paraformaldehyde, 0.022 g (0.10 mmol) of sodium triacetoxyborohydride and 40 µL (0.20 mmol) of hydrochloric acid (5-6N in isopropanol). The reaction mixture was stirred at room temperature for 12 hours. To the resulting mixture was added 0.006 g (0.07 mmol) of paraformaldehyde 0.042 g (0.20 mmol) of sodium triacetoxyborohydride and pH was adjusted to 6 with glacial acetic acid. The resulting mixture was stirred at room temperature for 2 hours. The reaction mixture was concentrated; the residue was dissolved in dichloromethane, washed with a saturated aqueous solution of sodium carbonate, saturated aqueous solution of sodium chloride, dried over sodium sulfate and evaporated. The free base was transformed into its hydrochloride salt to give 0.035 g of pure product.

Mp: 197-199° C.

NMR $^1$H (DMSO; 400 MHz)

δ (ppm): 9.38 (m, 1H), 9.12 (d, 1H), 8.28 (d, 1H), 8.01 (d, 1H), 7.40 (s, 1H), 7.32 (s, 1H), 7.20 (d, 1H), 5.61 (m, 1H), 5.02 (m, 1H), 4.08 (s, 3H), 4.06 (m, 1H), 3.10-2.95 (m, 4H), 2.40 (s, 3H)

Example 4

Compound No. 4 of Table 1

(+/−)-4-Chloro-N-[7-(4-fluoro-phenyl)-4-oxo-2-pyrimidin-4-yl-4,5,6,7,8,9-hexahydro-1,4a,7-triaza-benzocyclohepten-9-yl]-2-methoxy-benzamide A mixture containing 0.035 g (0.08 mmol) of (+/−)-4-chloro-2-methoxy-N-(4-oxo-2-pyrimidin-4-yl-4,5,6,7,8,9-hexahydro-1,4a,7-triaza-benzocyclohepten-9-yl)-benzamide, 0.016 g (0.09 mmol) of 4-bromofluorobenzene, 0.009 g (0.10 mmol) of sodium tert-butoxide, 0.006 g (0.03 mmol) of tri-tert-butylphosphine and 0.007 g (0.01 mmol) of tris(dibenzylideneacetone)dipalladium(0) in 1.60 mL of anhydrous toluene under argon atmosphere was stirred under reflux for 4 h30. The reaction mixture was cooled, aqueous solution of sodium carbonate was added and the resulting solution extracted with dichloromethane. The combined extracts were washed with saturated aqueous sodium chloride, dried over sodium sulfate and evaporated. The crude product was purified by chromatography on silica gel eluting with a mixture of dichloromethane/methanol/aqueous ammonia solution (29%) in the proportions 90/10/1 to afford 0.016 g (38%) of the pure product as a powder.

Mp: 207-209° C.

NMR $^1$H (DMSO; 400 MHz)

δ (ppm): 9.50 (m, 1H), 9.40 (s, 1H), 9.18 (d, 1H), 8.31 (m, 1H), 8.08 (d, 1H), 7.41 (s, 1H), 7.32 (s, 1H), 7.25 (d, 1H), 7.12 (m, 4H), 5.68 (m, 1H), 5.15 (m, 1H), 4.06 (s, 3H), 4.01 (m, 2H), 3.91 (m, 1H), 3.48 (m, 1H), 3.20 (m, 1H).

Example 5

Compound No. 11 of Table 1

(−)-4-Chloro-2-methoxy-N-(4-oxo-2-pyrimidin-4-yl-4,5,6,7,8,9-hexahydro-1,4a,7-triaza-benzocyclohepten-9-yl)-benzamide 0.400 g (0.93 mmol) of (+/−)-4-chloro-2-methoxy-N-(4-oxo-2-pyrimidin-4-yl-4,5,6,7,8,9-hexahydro-1,4a,7-triaza-benzocyclohepten-9-yl)-benzamide was separated by chirale preparative HPLC (CHIRALPAK IA-H 20 μm,) eluting with a mixture of acetonitrile/ethanol in the proportions 9/1 to give 0.185 g of pure product obtained in the form of free base.

Mp: 247-249° C. $[\alpha]_D^{20}$=−42° (c=2.254., DMSO).

NMR $^1$H (DMSO; 400 MHz)

δ (ppm): 9.49 (s, 1H), 9.30 (m, 1H), 9.12 (d, 1H), 8.30 (m, 1H), 7.98 (d, 1H), 7.48 (s, 1H), 7.30 (s, 1H), 7.21 (d, 1H), 5.54 (m, 1H), 4.98 (m, 1H), 4.03 (s, 3H), 3.95 (m, 1H), 3.11 (m, 2H), 2.90 (m, 1H), 2.70 (m, 1H).

Example 6

Compound No. 12 of Table 1

(+)-4-Chloro-2-methoxy-N-(4-oxo-2-pyrimidin-4-yl-4,5,6,7,8,9-hexahydro-1,4a,7-triaza-benzocyclohepten-9-yl)-benzamide 0.400 g (0.93 mmol) of (+/−)-4-chloro-2-methoxy-N-(4-oxo-2-pyrimidin-4-yl-4,5,6,7,8,9-hexahydro-1,4a,7-triaza-benzocyclohepten-9-yl)-benzamide was separated by chirale preparative HPLC(CHIRALPAK IA-H 20 μm,) eluting with a mixture of acetonitrile/ethanol in the proportions 9/1 to give 0.170 g of pure product obtained in the form of free base.

Mp: 240-242° C. $[\alpha]_D^{20}$=+64° (c=3.276.DMSO).

NMR $^1$H (DMSO; 400 MHz)

δ (ppm): 9.49 (s, 1H), 9.30 (m, 1H), 9.12 (d, 1H), 8.30 (m, 1H), 7.98 (d, 1H), 7.48 (s, 1H), 7.30 (s, 1H), 7.21 (d, 1H), 5.54 (m, 1H), 4.98 (m, 1H), 4.03 (s, 3H), 3.95 (m, 1H), 3.11 (m, 2H), 2.90 (m, 1H), 2.70 (m, 1H).

Example 7

Compound No. 15 of Table 1

(−)-4-Chloro-2-methoxy-N-(7-methyl-4-oxo-2-pyrimidin-4-yl-4,5,6,7,8,9-hexahydro-1,4a,7-triaza-benzocyclohepten-9-yl)benzamide By analogy with the method described in example 3, using (−)-4-chloro-2-methoxy-N-(4-oxo-2-pyrimidin-4-yl-4,5,6,7,8,9-hexahydro-1,4a,7-triaza benzocyclohepten-9-yl)-benzamide (example 5) in place of (+/−)-4-chloro-2-methoxy-N-(4-oxo-2-pyrimidin-4-yl-4,5,6,7,8,9-hexahydro-1,4a,7-triaza-benzocyclohepten-9-yl)-benzamide, the compound was obtained as a powder (69%).

Mp: 239-241° C. $[\alpha]_D^{20}$=−72.57° (c=0.261, DMSO).

NMR $^1$H (DMSO; 400 MHz)

δ (ppm): 9.38 (m, 1H), 9.12 (d, 1H), 8.28 (d, 1H), 8.01 (d, 1H), 7.40 (s, 1H), 7.32 (s, 1H), 7.20 (d, 1H), 5.61 (m, 1H), 5.02 (m, 1H), 4.08 (s, 3H), 4.06 (m, 1H), 3.10-2.95 (m, 4H), 2.40 (s, 3H).

Example 8

Compound No. 16 of Table 1

(+)-4-Chloro-2-methoxy-N-(7-methyl-4-oxo-2-pyrimidin-4-yl-4,5,6,7,8,9-hexahydro-1,4a,7-triaza-benzocyclohepten-9-yl)benzamide By analogy with the method described in example 3, using (+)-4-chloro-2-methoxy-N-(4-oxo-2-pyrimidin-4-yl-4,5,6,7,8,9-hexahydro-1,4a,7-triaza benzocyclohepten-9-yl)-benzamide (example 6) in place of (+/−)-4-chloro-2-methoxy-N-(4-oxo-2-pyrimidin-4-yl-4,5,6,7,8,9-hexahydro-1,4a,7-triaza-benzocyclohepten-9-yl)-benzamide, the compound was obtained as a powder (59%).

Mp: 232-234° C. $[\alpha]_D^{20}$=+73.58° (c=0.212, DMSO).

NMR $^1$H (DMSO; 400 MHz)

δ (ppm): 9.38 (m, 1H), 9.12 (d, 1H), 8.28 (d, 1H), 8.01 (d, 1H), 7.40 (s, 1H), 7.32 (s, 1H), 7.20 (d, 1H), 5.61 (m, 1H), 5.02 (m, 1H), 4.08 (s, 3H), 4.06 (m, 1H), 3.10-2.95 (m, 4H), 2.40 (s, 3H).

Example 9

Compound No. 13 of Table 1

(+/−)-9-(4-Methoxy-benzylamino)-4-oxo-2-pyrimidin-4-yl-5,6,8,9-tetrahydro-4H-1,4a,7-triaza-benzocycloheptene-7-carboxylic acid ethyl ester 9.1 4-Oxo-2-pyrimidin-4-yl-5,6,8,9-tetrahydro-4H-1,4a,7-triaza-benzocycloheptene-7-carboxylic acid ethyl ester To a suspension of 13.4 g (60.45 mmol) of 5-amino-2,3,6,7-tetrahydro-[1,4]diazepine-1-carboxylic acid ethyl ester monohydrochloride (synthesis as described in WO9716430) in 50 mL of ethanol was added 10.29 g (74.50 mmol) of potassium carbonate. The reaction mixture was stirred at room temperature for 10 min, 14.47 g (74.50 mmol) of ethyl 3-(4-pyrimidinyl)-3-oxopropionate was added and the resulting mixture was stirred under reflux for 2.5 hours. The cooled solution was evaporated to remove solvent. The mixture was dissolved with water and diethyl ether. After stirring, the resulting solid was filtered, washed with water and diethyl ether to afford 8.80 g (46%) of the desired compound as a powder.

Mp: 144-146° C.

NMR $^1$H (DMSO-d$^6$; 400 MHz)

δ (ppm): 9.34 (s, 1H), 9.06 (d, 1H), 8.28 (d, 1H), 7.29 (s, 1H), 4.42 (m, 2H), 4.10 (m, 2H), 3.72 (m, 4H), 3.29 (m, 2H), 1.20 (t, 3H).

9.2 (+/−)-9-Bromo-4-oxo-2-pyrimidin-4-yl-5,6,8,9-tetrahydro-4H-1,4a,7-triaza-benzocycloheptene-7-carboxylic acid ethyl ester To a solution of 4.5 g (14.27 mmol) of 4-oxo-2-pyrimidin-4-yl-5,6,8,9-tetrahydro-4H-1,4a,7-triaza-benzocycloheptene-7-carboxylic acid ethyl ester in dry tetrahydrofuran (140 mL) under argon at −30° C. was added 15.70 mL (15.70 mmol) of lithium bis(trimethylsilyl)amide (1M in tetrahydrofuran). The solution was stirred at −30° C. for 5 min and 0.77 mL (14.98 mmol) of bromine was added. The reaction was stirred at −30° C. to room temperature during 3 hours. The mixture was quenched with the addition of a saturated solution of ammonium chloride and extracted with ethyl acetate.

The organic phase was dried over sodium sulfate and concentrated. The residue was purified by flash chromatography (dichloromethane with 1 to 3% of methanol) to afford 2.6 g (46%) of product.

NMR $^1$H (DMSO-d$^6$; 400 MHz)

δ (ppm): 9.35 (s, 1H), 9.08 (d, 1H), 8.23 (d, 1H), 7.35 (s, 1H), 5.68 (m, 1H), 5.21 (m, 1H), 4.31 (m, 3H), 4.11 (m, 2H), 3.95 (m, 2H), 1.21 (t, 3H).

9.3 (+/−)-9-(4-Methoxy-benzylamino)-4-oxo-2-pyrimidin-4-yl-5,6,8,9-tetrahydro-4H-1,4a,7-triaza-benzocycloheptene-7-carboxylic acid ethyl ester To a suspension of 8.20 g (20.80 mmol) of 9-bromo-4-oxo-2-pyrimidin-4-yl-5,6,8,9-tetrahydro-4H-1,4a,7-triaza-benzocycloheptene-7-carboxylic acid ethyl ester in 208 mL of toluene was added 8.56 g (62.40 mmol) of 4-methoxybenzylamine and 14.77 mL (208.00 mmol) of dimethylsulfoxide. The reaction mixture was stirred at 85° C. for 15 hours. The cooled solution was evaporated to remove solvent. The mixture was quenched with the addition of a saturated solution of ammonium chloride and extracted with dichloromethane, washed with saturated solution of sodium chloride. The organic phase was dried over sodium sulfate and concentrated. The residue was purified by flash chromatography (dichloromethane methanol/ammonia 98/2/0.2 to 97/3/0.3) to afford 5.80 g (62%) of product.

Mp: 217-219° C.

NMR $^1$H (DMSO-d$^6$; 400 MHz)

δ (ppm): 9.31 (s, 1H), 9.04 (d, 1H), 8.28 (d, 1H), 7.21 (m, 3H), 6.82 (d, 2H), 4.72 (m, 1H), 4.38 (m, 1H), 4.20 (m, 1H), 4.02 (m, 2H), 3.78 (m, 5H), 3.70 (s, 3H), 3.52 (m, 1H), 1.12 (t, 3H)

Example 10

Compound No. 19 of Table 1

(+/−)-9-(4-Bromo-benzoylamino)-4-oxo-2-pyrimidin-4-yl-5,6,8,9-tetrahydro-4H-1,4a,7-triaza-benzocycloheptene-7-carboxylic acid ethyl ester 10.1 (+/−)-9-Amino-4-oxo-2-pyrimidin-4-yl-5,6,8,9-tetrahydro-4H-1,4a,7-triaza-benzocycloheptene-7-carboxylic acid ethyl ester To a solution of 10.75 g (23.86 mmol) of 9-(4-methoxybenzylamino)-4-oxo-2-pyrimidin-4-yl-5,6,8,9-tetrahydro-4H-1,4a,7-triaza-benzocycloheptene-7-carboxylic acid ethyl ester acetonitrile/water (160/80 mL) was added 26.16 g (47.73 mmol) of ammonium cerium nitrate. The reaction was stirred at room temperature for 2 hours. 13.08 g (23.86 mmol) of ammonium cerium nitrate was added and the reaction was stirred at room temperature for 0.5 hours. After an acido-basic work-up and extraction with dichloromethane, the organic phase was washed with a saturated solution of sodium chloride, dried over sodium sulfate and concentrated to afford 5.15 g (65%) of a powder.

Mp: 185-187° C.

NMR $^1$H (DMSO-d$^6$; 400 MHz)

δ (ppm): 9.32 (s, 1H), 9.05 (d, 1H), 8.44 (d, 1H), 7.28 (s, 1H), 4.89 (m, 1H), 4.40 (m, 1H), 4.12-4.01 (m, 3H), 3.90 (m, 1H), 3.75 (m, 1H), 3.50 (m, 2H), 2.32 (br s, 2H), 1.15 (t, 3H)

10.2 (+/−)-9-(4-Bromo-benzoylamino)-4-oxo-2-pyrimidin-4-yl-5,6,8,9-tetrahydro-4H-1,4a,7-triaza-benzocycloheptene-7-carboxylic acid ethyl ester By analogy with the method described in example 1 (step 1.8), using 4-bromo-benzoic acid in place of 4-chloro-2-methoxy-benzoic acid, the compound, 0.062 g (11%), was obtained as a white powder.

Mp: 259-261° C.

NMR $^1$H (DMSO-d$^6$; 400 MHz)

δ (ppm): 9.32 (s, 1H), 9.18 (br s, 1H), 9.01 (d, 1H), 8.15 (m, 1H), 7.96 (m, 2H), 7.80 (m, 2H), 7.32 (s, 1H), 5.55 (m, 1H), 5.02 (m, 1H), 4.18 (m, 2H), 4.02 (m, 2H), 3.75 (m, 1H), 3.48 (m, 2H), 1.15 (m, 3H)

Example 11

Compound No. 28 of Table 1

9-[4-(1-Methyl-1H-pyrazol-4-yl)-benzoylamino]-4-oxo-2-pyrimidin-4-yl-5,6,8,9-tetrahydro-4H-1,4a,7-triaza-benzocycloheptene-7-carboxylic acid ethyl ester A mixture containing 0.145 g (0.28 mmol) of 9-(4-bromo-benzoylamino)-4-oxo-2-pyrimidin-4-yl-5,6,8,9-tetrahydro-4H-1,4a,7-triaza-benzocycloheptene-7-carboxylic acid ethyl ester (example 10), 0.082 g (0.40 mmol) of 1-methyl-1H-pyrazole-4-boronic acid pinacol ester, 0.35 mL (0.71 mmol) of sodium carbonate (solution 2M), 0.065 g (0.06 mmol) of tetrakis(tri-phenylphosphine)palladium in 5.60 mL of toluene/EtOH (10/1) under argon atmosphere was stirred at 90° C. for 15 hours. The reaction mixture was cooled, aqueous saturated solution of sodium carbonate was added and the resulting solution extracted with dichloromethane. The combined extracts were washed with saturated aqueous sodium chloride, dried over sodium sulfate and evaporated. The crude product was purified by chromatography on silica gel eluting with a mixture of dichloromethane/methanol/aqueous ammonia solution (29%) in the proportions 98/2/0.2 to 97/3/0.3 to afford 0.088 g (76%) of the pure product as a white powder.

Mp: 265-267° C.

NMR $^1$H (DMSO; 400 MHz)

δ (ppm): 9.32 (s, 1H), 9.00 (m, 2H), 8.30 (d, 1H), 8.18 (br s, 1H), 8.00 (m, 3H), 7.78 (d, 2H), 7.32 (s, 1H), 5.58 (m, 1H), 5.05 (m, 1H), 4.18 (m, 2H), 4.05 (m, 3H), 3.91 (s, 3H), 3.75 (m, 1H), 3.48 (m, 1H), 1.18 (m, 3H).

Example 12

Compound No. 25 of Table 1

(+/−)-9-Benzylamino-4-oxo-2-pyrimidin-4-yl-5,6,8,9-tetrahydro-4H-1,4a,7-triaza-benzocycloheptene-7-carboxylic acid ethyl ester hydrochloride (1:1)

To a solution of 0.120 g (0.36 mmol) of 9-amino-4-oxo-2-pyrimidin-4-yl-5,6,8,9-tetrahydro-4H-1,4a,7-triaza-benzocycloheptene-7-carboxylic acid ethyl ester in 3.6 ml of dichloromethane was added 0.041 g (0.38 mmol) of benzaldehyde, 0.192 g (0.91 mmol) of sodium triacetoxyborohydride and few drops of glacial acetic acid. The reaction mixture was stirred at room temperature for 15 hours. The residue was dissolved in dichloromethane and a saturated aqueous solution of sodium carbonate, extracted with dichloromethane and washed with saturated aqueous solution of sodium chloride, dried over sodium sulfate and evaporated. The crude product was purified by chromatography on silica gel eluting with a mixture of dichloromethane/methanol/aqueous ammonia solution (29%) in the proportions 97/3/0.3 to give 0.145 g (95%) of pure product. The free base was transformed into its hydrochloride salt.

Mp: 186-188° C.
NMR $^1$H (DMSO; 400 MHz)
δ (ppm): 9.40 (s, 1H), 9.11 (d, 1H), 8.48 (d, 1H), 7.60 (m, 2H), 7.48 (m, 3H), 7.38 (s, 1H), 5.29 (m, 1H), 5.15 (m, 1H), 4.50 (m, 1H), 4.37 (m, 2H), 4.10 (m, 3H), 3.82 (m, 1H), 3.60 (m, 1H), 3.40 (m, 1H), 1.18 (t, 3H).

Example 13

Compound No. 27 of Table 1

(+/−)-9-Benzylamino-2-pyrimidin-4-yl-6,7,8,9-tetrahydro-5H-1,4a,7-triaza-benzocyclohepten-4-one hydrobromide (1:2)

To a solution of 0.090 g (0.21 mmol) of 9-benzylamino-4-oxo-2-pyrimidin-4-yl-5,6,8,9-tetrahydro-4H-1,4a,7-triaza-benzocycloheptene-7-carboxylic acid ethyl ester dissolved in 3.00 mL of glacial acetic acid was added 0.75 mL (4.28 mmol) of hydrobromic acid (33 wt % solution in glacial acetic acid). The resulting mixture was stirred at 80° C. for 16 hours, cooled and evaporated to dryness. Toluene was added to the residue and evaporated. Ethanol was added to the residue and evaporated. The crude was triturated with diethyl ether and dichloromethane and filtered to afford 0.083 g (76%) of the product as a powder.

Mp: 210-212° C.
NMR $^1$H (DMSO; 400 MHz)
δ (ppm): 9.40 (s, 1H), 9.12 (d, 1H), 8.41 (d, 1H), 7.64 (m, 2H), 7.50 (m, 3H), 7.41 (s, 1H), 5.40 (m, 1H), 5.22 (m, 1H), 4.40 (m, 2H), 4.11 (m, 3H), 3.78 (m, 2H), 3.60 (m, 1H), 3.31 (m, 1H).

Example 14

Compound No. 33 of Table 1

(+/−)-9-(2,4-Dimethoxy-benzoylamino)-4-oxo-2-pyridin-4-yl-5,6,8,9-tetrahydro-4H-1,4a,7-triaza-benzocycloheptene-7-carboxylic acid ethyl ester 14.1 4-Oxo-2-pyridin-4-yl-5,6,8,9-tetrahydro-4H-1,4a,7-triaza-benzocycloheptene-7-carboxylic acid ethyl ester By analogy with the method described in example 9 (step 9.1), using 3-oxo-3-pyridin-4-yl-propionic acid ethyl ester in place of ethyl 3-(4-pyrimidinyl)-3-oxopropionate, 9.45 g (44%) of the compound was obtained as a white powder.

Mp: 191-193° C.
NMR $^1$H (DMSO-d$^6$; 400 MHz)
δ (ppm): 8.76 (d, 2H), 8.02 (d, 2H), 7.12 (s, 1H), 4.42 (m, 2H), 4.11 (q, 2H), 3.75 (m, 4H), 3.28 (m, 2H), 1.21 (t, 3H).

14.2 9-Amino-4-oxo-2-pyridin-4-yl-5,6,8,9-tetrahydro-4H-1,4a,7-triaza-benzocycloheptene-7-carboxylic acid ethyl ester By analogy with the method described in example 9 (step 9.2, step 9.3, step 10.1), using 4-oxo-2-pyridin-4-yl-5,6,8,9-tetrahydro-4H-1,4a,7-triaza-benzocycloheptene-7-carboxylic acid ethyl ester in place of 4-oxo-2-pyrimidin-4-yl-5,6,8,9-tetrahydro-4H-1,4a,7-triaza-benzocycloheptene-7-carboxylic acid ethyl ester, the compound was obtained as a white powder.

Mp: 171-173° C.
NMR $^1$H (DMSO-d$^6$; 400 MHz)
δ (ppm): 8.72 (d, 2H), 8.11 (d, 2H), 7.29 (s, 1H), 4.85 (m, 1H), 4.40 (m, 1H), 4.08 (m, 3H), 3.90 (m, 1H), 3.75 (m, 1H), 3.48 (m, 2H), 2.35 (br s, 2H), 1.18 (t, 3H)

14.3 (+/−)-9-(2,4-Dimethoxy-benzoylamino)-4-oxo-2-pyridin-4-yl-5,6,8,9-tetrahydro-4H-1,4a,7-triaza-benzocycloheptene-7-carboxylic acid ethyl ester By analogy with the method described in example 1 (step 1.8), using 9-amino-4-oxo-2-pyridin-4-yl-5,6,8,9-tetrahydro-4H-1,4a,7-triaza-benzocycloheptene-7-carboxylic acid ethyl ester and 2,4-dimethoxy-benzoic acid in place of (+/−)-9-amino-4-oxo-2-pyrimidin-4-yl-5,6,8,9-tetrahydro-4H-1,4a,7-triaza benzocycloheptene-7-carboxylic acid ethyl ester hydrobromide (1:1) and 4-chloro-2-methoxy-benzoic acid, the compound, 0.103 g (76%), was obtained as a white powder.

Mp: 231-233° C.
NMR $^1$H (DMSO-d$^6$; 400 MHz)
δ (ppm): 9.30 (m, 1H), 8.80 (d, 2H), 8.08 (d, 2H), 8.01 (d, 1H), 7.21 (s, 1H), 6.80 (m, 1H), 6.72 (d, 1H), 5.59 (m, 1H), 5.02 (m, 1H), 4.28 (m, 1H), 4.07 (m, 4H), 3.98 (s, 3H), 3.87 (s, 3H), 3.51 (m, 1H), 3.39 (m, 1H), 1.14 (m, 3H).

Example 15

Compound No. 29 of Table 1

4-Amino-5-chloro-2-methoxy-N-(4-oxo-2-pyrimidin-4-yl-4,5,6,7,8,9-hexahydro-1,4a,7-triaza-benzocyclohepten-9-yl)-benzamide To a solution of 0.040 g (0.199 mmol) of 4amino-5-chloro-2-methoxy-benzoic acid dissolved in 5 mL of anhydrous dimethylformamide was added 0.06 mL (0.43 mmol) of triethylamine, 0.077 g (0.20 mmol) of O-(benzotriazol-1-yl)-N,N,N'N,'-tetramethyluroniumhexafluorophosphate (HBTU). The resulting mixture was stirred at room temperature for 5 min and added slowly at −10° C. to a solution of 0.090 g (0.21 mmol) of (+/−)-9-amino-2-pyrimidin-4-yl-6,7,8,9-tetrahydro-5H-1,4a,7-triaza-benzocyclohepten-4-one dihydrobromide (2:1) dissolved in a mixture of 5 mL of anhydrous dimethylformamide and 0.09 mL (0.64 mmol) of triethylamine. The resulting mixture slowly increases to room temperature and was stirred for 16 hours. After evaporation, the reaction mixture was diluted in dichloromethane and a saturated aqueous solution of sodium carbonate. The organic phase was washed saturated aqueous sodium chloride, dried over sodium sulfate and evaporated to dryness. The residue was chromatographed on silica gel eluting with a mixture of dichloromethane/methanol/aqueous ammonia solution (29%) in the proportions 97/3/0.3 to afford 0.022 g (23%) of the pure product as a powder.

Mp: 277-279° C.
NMR $^1$H (DMSO-d$^6$; 400 MHz)
δ (ppm): 9.70 (br s, 2H), 9.40 (s, 1H), 9.25 (m, 1H), 9.20 (d, 1H), 8.28 (d, 1H), 7.85 (s, 1H), 7.48 (s, 1H), 6.62 (s, 1H), 6.18 (br s, 1H), 5.75 (m, 1H), 5.25 (m, 1H), 4.06 (m, 1H), 3.96 (s, 3H), 3.61 (m, 2H), 3.40 (m, 1H), 3.18 (m, 1H).

Example 16

Compound No. 36 of Table 1

(+/−)-9-[(4-Chloro-2-methoxy-benzoyl)-methyl-amino]-4-oxo-2-pyridin-4-yl-5,6,8,9-tetrahydro-4H-1,4a,7-triaza-benzocycloheptene-7-carboxylic acid ethyl ester

16.1 9-[(4-Methoxy-benzyl)-methyl-amino]-4-oxo-2-pyridin-4-yl-5,6,8,9-tetrahydro-4H-1,4a,7-triaza-benzocycloheptene-7-carboxylic acid ethyl ester By analogy with the method described in example 12 using 9-(4-methoxy-benzylamino)-4-oxo-2-pyridin-4-yl-5,6,8,9-tetrahydro-4H-1,4a,7-triaza-benzocycloheptene-7-carboxylic acid ethyl ester (example 9) in place of 9-amino-4-oxo-2-pyrimidin-4-yl-5,6,8,9-tetrahydro-4H-1,4a,7-triaza-benzocycloheptene-7-carboxylic acid ethyl ester and formaldehyde (37%) in place of benzaldehyde, the compound was obtained as a solid oil. The compound was used as such in the next step.

16.2 (+/−)-9-Methylamino-4-oxo-2-pyridin-4-yl-5,6,8,9-tetrahydro-4H-1,4a,7-triaza-benzocycloheptene-7-carboxylic acid ethyl ester By analogy with the method described in example 10 (step 10.1) using 9-[(4-methoxy-benzyl)-methyl-amino]-4-oxo-2-pyridin-4-yl-5,6,8,9-tetrahydro-4H-1,4a,7-triaza-benzocycloheptene-7-carboxylic acid ethyl ester in place of 9-(4-methoxy-benzylamino)-4-oxo-2-pyrimidin-4-yl-5,6,8,9-tetrahydro-4H-1,4a,7-triaza-benzocycloheptene-7-carboxylic acid ethyl ester.

NMR $^1$H (DMSO-d$^6$; 400 MHz)

δ (ppm): 8.72 (d, 2H), 8.08 (d, 2H), 7.18 (s, 1H), 4.78 (m, 1H), 4.28 (m, 1H), 4.08 (m, 3H), 3.86 (m, 1H), 3.62 (m, 3H), 2.41 (s, 3H), 1.18 (t, 3H).

16.3 (+/−)-9-[(4-Chloro-2-methoxy-benzoyl)-methyl-amino]-4-oxo-2-pyridin-4-yl-5,6,8,9-tetrahydro-4H-1,4a,7-triaza-benzocycloheptene-7-carboxylic acid ethyl ester By analogy with the method described in example 1 (step 1.8), using (+/−)-9-methylamino-4-oxo-2-pyridin-4-yl-5,6,8,9-tetrahydro-4H-1,4a,7-triaza-benzocycloheptene-7-carboxylic acid ethyl ester in place of (+/−)-9-amino-4-oxo-2-pyrimidin-4-yl-5,6,8,9-tetrahydro-4H-1,4a,7-triaza benzocycloheptene-7-carboxylic acid ethyl ester hydrobromide (1:1), the compound, 0.075 g (77%), was obtained as a white powder.

Mp: 232-234° C.

NMR $^1$H (DMSO-d$^6$; 400 MHz)

δ (ppm): 8.75 (m, 2H), 8.01 (m, 2H), 7.28 (s, 1H), 7.18 (m, 3H), 5.94 (m, 1H), 5.10 (m, 1H), 4.22-3.81 (m, 9H), 3.41 (m, 1H), 3.02 (s, 3H), 1.16 (m, 3H).

A list of chemical structures and physical data for compounds of the aforementioned formula (I), illustrating the present invention, is given in table 1. The compounds have been prepared according to the methods of the examples. In the table, Me represents a methyl group, Et represents an ethyl group, (Rot.) indicates the levorotatory or dextrorotatory properties of the enantiomeric compound, (dec.) indicates the decomposition of the compound.

TABLE 1

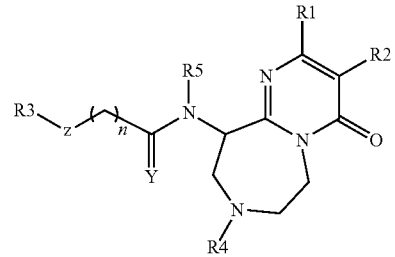

(I)

| No. | Rot | R3 | Z | R1 | R4 | R5 | R2 | Y | n | Mp ° C. | salt |
|---|---|---|---|---|---|---|---|---|---|---|---|
| 1 | (+/−) | Cl-（2-OMe,4-Me-phenyl） | bond | pyrimidin-4-yl | CO$_2$Et | H | H | O | 0 | 175-177 | Free base |
| 2 | (+/−) | Cl-（2-OMe,4-Me-phenyl） | bond | pyrimidin-4-yl | H | H | H | O | 0 | 256-258 | HCl (1:1) |
| 3 | (+/−) | Cl-（2-OMe,4-Me-phenyl） | bond | pyrimidin-4-yl | Me | H | H | O | 0 | 197-199 | HCl (1:1) |

TABLE 1-continued
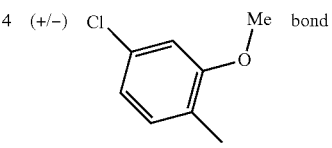
(I)
| No. | Rot | R3 | Z | R1 | R4 | R5 | R2 | Y | n | Mp °C. | salt |
|---|---|---|---|---|---|---|---|---|---|---|---|
| 4 | (+/−) | 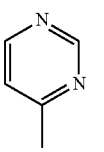 | bond | 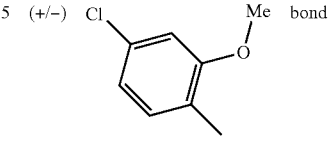 | 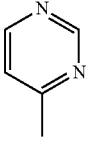 | H | H | O | 0 | 207-209 | Free base |
| 5 | (+/−) | 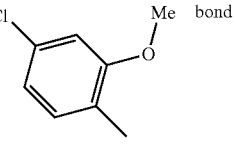 | bond | 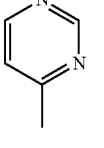 | 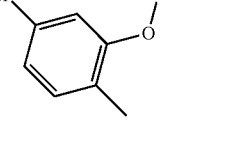 | H | H | O | 0 | 187-190 | HCl (1:1) |
| 6 | (+/−) | 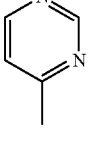 | bond | 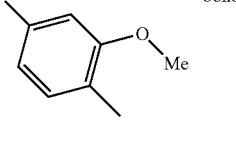 | 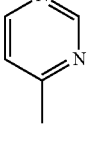 | H | H | O | 0 | 194-196 | HCl (1:1) |
| 7 | (+/−) | 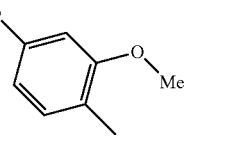 | bond | 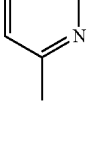 | 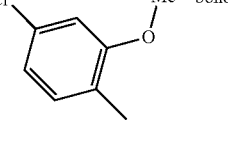 | H | H | O | 0 | 243-245 | HCl (1:1) |
| 8 | (+/−) | 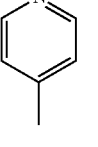 | bond | | H | H | H | O | 0 | 225-227 | HCl (1:1) |
| 9 | (+/−) | | bond | | H | H | H | O | 0 | 227-229 | HCl (1:1) |
| 10 | (+/−) | | bond | | H | H | H | O | 0 | 233-236 | HCl (1:1) |

TABLE 1-continued
(I)
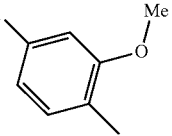
| No. | Rot | R3 | Z | R1 | R4 | R5 | R2 | Y | n | Mp °C. | salt |
|---|---|---|---|---|---|---|---|---|---|---|---|
| 11 | (−) | 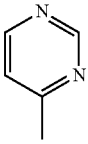 | bond | 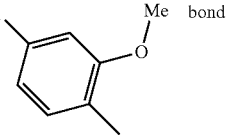 | H | H | H | O | 0 | 247-249 | Free base |
| 12 | (+) | 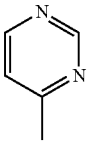 | bond | 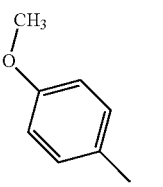 | H | H | H | O | 0 | 240-242 | Free base |
| 13 | (+/−) | 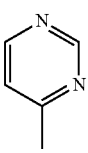 | bond | 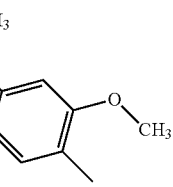 | CO$_2$Et | H | H | H, H | 0 | 217-219 | HCl (1:1) |
| 14 | (+/−) | 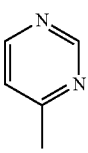 | bond | 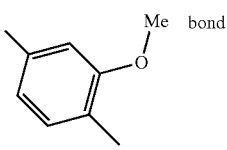 | CO$_2$Et | H | H | H, H | 0 | 144-146 | Free base |
| 15 | (−) | 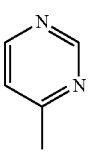 | bond | 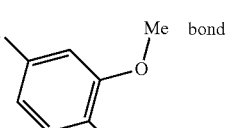 | Me | H | H | O | 0 | 239-241 | Free base |
| 16 | (+) | 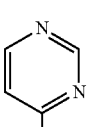 | bond | 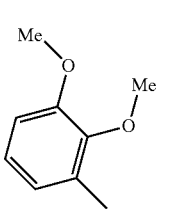 | Me | H | H | O | 0 | 232-234 | Free base |
| 17 | (+/−) | 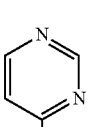 | bond |  | CO2Et | H | H | O | 0 | 204-206 | Free base |

TABLE 1-continued (I)

| No. | Rot | R3 | Z | R1 | R4 | R5 | R2 | Y | n | Mp °C. | salt |
|---|---|---|---|---|---|---|---|---|---|---|---|
| 18 | (+/−) | CF3, Me-O-phenyl | bond | pyrimidinyl | CO2Et | H | H | O | 0 | 206-208 | Free base |
| 19 | (+/−) | Br-phenyl | bond | pyrimidinyl | CO2Et | H | H | O | 0 | 259-261 | Free base |
| 20 | (+/−) | F, CF3-phenyl | bond | pyrimidinyl | CO2Et | H | H | O | 0 | 250-252 | Free base |
| 21 | (+/−) | Me-O-phenyl | bond | pyrimidinyl | CO2Et | H | H | O | 0 | 182-184 | Free base |
| 22 | (+/−) | Me-O-phenyl | bond | pyrimidinyl | H | H | H | O | 0 | 213-216 | HCl (1:1) |
| 23 | (+/−) | Br, Me-O-phenyl | bond | pyrimidinyl | H | H | H | O | 0 | 217-220 | Free base |
| 24 | (+/−) | O-Me, O-Me-phenyl | bond | pyrimidinyl | H | H | H | O | 0 | 245-247 | HCl (1:1) |
| 25 | (+/−) | phenyl | bond | pyrimidinyl | CO2Et | H | H | H, H | 0 | 186-188 | HCl (1:1) |

TABLE 1-continued
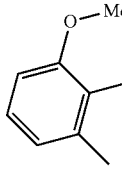
(I)
| No. | Rot | R3 | Z | R1 | R4 | R5 | R2 | Y | n | Mp °C. | salt |
|---|---|---|---|---|---|---|---|---|---|---|---|
| 26 | (+/−) | 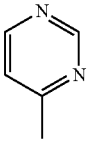 | bond | 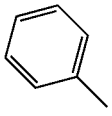 | Me | H | H | O | 0 | 195-197 | HCl (1:1) |
| 27 | (+/−) | 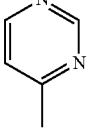 | bond | 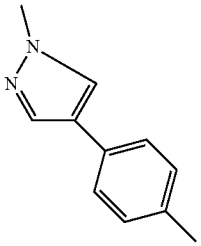 | H | H | H | H, H | 0 | 210-212 | HBr (1:2) |
| 28 | (+/−) | 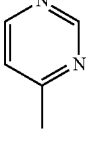 | bond | 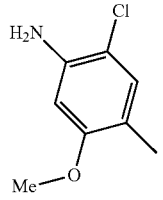 | CO2Et | H | H | O | 0 | 265-267 | Free base |
| 29 | (+/−) | 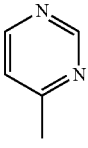 | bond | 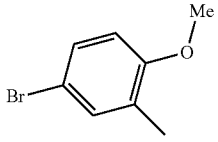 | H | H | H | O | 0 | 277-279 | Free base |
| 30 | (+/−) | 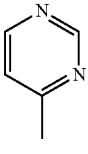 | bond | 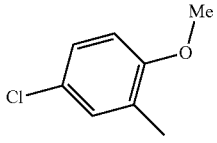 | Me | H | H | O | 0 | 204-206 | Free base |
| 31 | (+/−) | 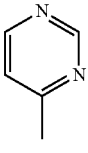 | bond | 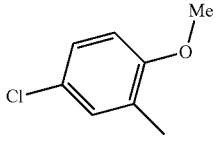 | Me | H | H | O | 0 | 212-214 | Free base |
| 32 | (+/−) | 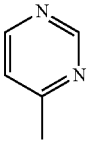 | bond | | H | H | H | O | 0 | 214-216 | HCl (1:1) |

TABLE 1-continued
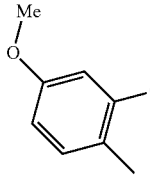
(I)
| No. | Rot | R3 | Z | R1 | R4 | R5 | R2 | Y | n | Mp °C. | salt |
|---|---|---|---|---|---|---|---|---|---|---|---|
| 33 | (+/−) |  | bond | 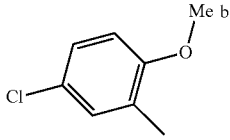 | CO2Et | H | H | O | 0 | 231-233 | Free base |
| 34 | (+/−) | 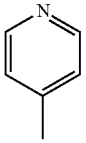 | bond | 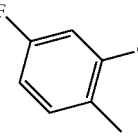 | CO2Et | H | H | O | 0 | 205-207 | Free base |
| 35 | (+/−) |  | bond | 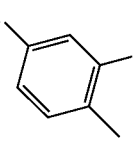 | CO2Et | H | H | O | 0 | 210-212 | Free base |
| 36 | (+/−) | 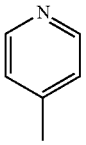 | bond | 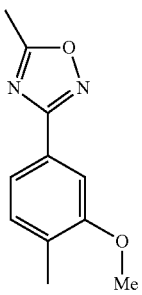 | CO2Et | Me | H | O | 0 | 232-234 | Free base |
| 37 | (+/−) | 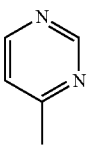 | bond | 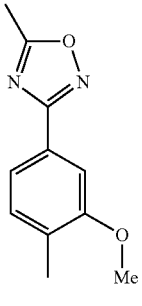 | H | H | H | O | 0 | 203-205 | Free base |
| 38 | (+/−) | 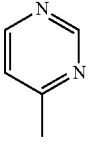 | bond |  | Me | H | H | O | 0 | 157-159 | Free base |

TABLE 1-continued
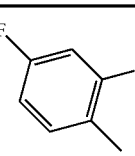
(I)
| No. | Rot | R3 | Z | R1 | R4 | R5 | R2 | Y | n | Mp °C. | salt |
|---|---|---|---|---|---|---|---|---|---|---|---|
| 39 | (+/−) | 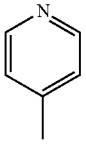 | bond | 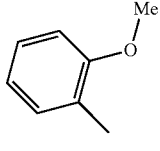 | Me | H | H | O | 0 | 216-218 | HCl (1:1) |
| 40 | (+/−) | 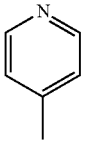 | bond | 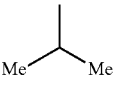 | 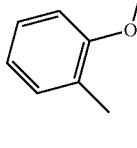 | H | H | O | 0 | 220-222 | HCl (1:1) |
| 41 | (+/−) | 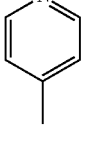 | bond | 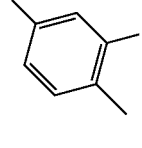 | H | H | H | O | 0 | 234-236 | HCl (1:1) |
| 42 | (+/−) | 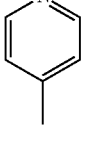 | bond | 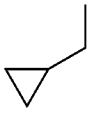 | 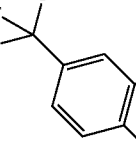 | H | H | O | 0 | 212-214 | HCl (1:1) |
| 43 | (+/−) | 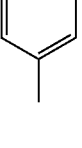 | bond | 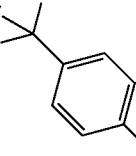 | H | H | H | O | 0 | 228-230 | HCl (1:1) |
| 44 | (+/−) | 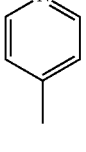 | bond | 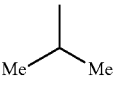 | 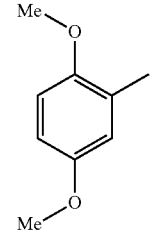 | H | H | O | 0 | 204-206 | HCl (1:1) |
| 45 | (+/−) | 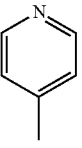 | bond | 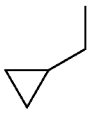 | 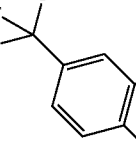 | H | H | O | 0 | 239-241 | HCl (1:1) |

TABLE 1-continued

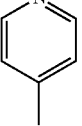

(I)

| No. | Rot | R3 | Z | R1 | R4 | R5 | R2 | Y | n | Mp °C. | salt |
|---|---|---|---|---|---|---|---|---|---|---|---|
| 46 | (+/−) | 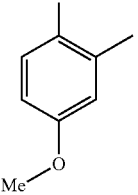 | bond | 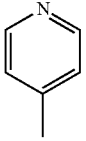 | H | H | H | O | 0 | 214-216 | HCl (1:1) |
| 47 | (+/−) | 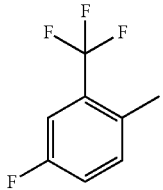 | bond | 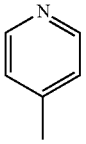 | H | H | H | O | 0 | 231-233 | HCl (1:1) |
| 48 | (+/−) | 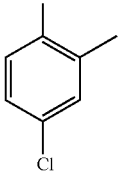 | bond | 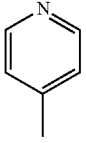 | H | H | H | O | 0 | 234-236 | HCl (1:1) |
| 49 | (+/−) | 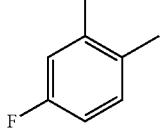 | bond | 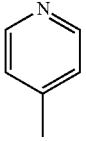 | Me | H | H | O | 0 | 215-217 | HCl (1:1) |
| 50 | (+/−) | 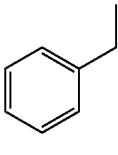 | bond | 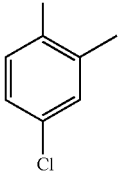 | H | H | H | O | 0 | 198-200 | HCl (1:1) |

Test Example

Inhibitory Activity of the Medicament of the Present Invention Against GSK3β

Four different protocols can be used.

In a first protocol: 7.5 μM of prephosphorylated GS1 peptide and 10 μM ATP (containing 300,000 cpm of $^{33}$P-ATP) were incubated in 25 mM Tris-HCl, pH 7.5, 0.6 mM DTT, 6 mM $MgCl_2$, 0.6 mM EGTA, 0.05 mg/ml BSA buffer for 1 hour at room temperature in the presence of GSK3beta (total reaction volume: 100 microliters).

In a second protocol: 4.1 μM of prephosphorylated GS1 peptide and 42 μM ATP (containing 260,000 cpm $^{33}$P-ATP) were incubated in 80 mM Mes-NaOH, pH 6.5, 1 mM Mg acetate, 0.5 mM EGTA, 5 mM 2-mercaptoethanol, 0.02%

Tween 20, 10% glycerol buffer for 2 hours at room temperature in the presence of GSK3beta.

In a third protocol: 7.5 µM of prephosphorylated GS1 peptide and 10 µM ATP (containing 300,000 cpm of $^{33}$P-ATP) were incubated in 50 mM Hepes, pH 7.2, 1 mM DTT, 1 mM MgCl$_2$, 1 mM EGTA, 0.01% Tween 20 buffer for one hour at room temperature in the presence of GSK3beta (total reaction volume: 100 microliters).

In a fourth protocol: 7.5 µM of prephosphorylated GS1 peptide and 10 µM ATP (containing 300,000 cpm of $^{33}$P-ATP) were incubated in 50 mM Hepes, pH 7.2, 1 mM DTT, 1 mM MgCl$_2$, 1 mM EGTA, 0.01% Tween 20 buffer for 90 minutes at room temperature in the presence of commercial GSK3beta (Millipore) (total reaction volume: 100 microliters).

Inhibitors were solubilised in DMSO (final solvent concentration in the reaction medium, 1%).

The reaction was stopped with 100 microliters of a solution made of 25 g polyphosphoric acid (85% P$_2$O$_5$), 126 ml 85% H$_3$PO$_4$, H$_2$O to 500 ml and then diluted to 1:100 before use. An aliquot of the reaction mixture was then transferred to Whatman P81 cation exchange filters and rinsed with the solution described above. Incorporated $^{33}$P radioactivity was determined by liquid scintillation spectrometry.

The phosphorylated GS-1 peptide had the following sequence: NH2-YRRAAVPPSPSLSRHSSPHQS(P)EDEE-COOH. (Woodgett, J. R. (1989) Analytical Biochemistry 180, 237-241.

The GSK3β inhibitory activity of the compounds of the present invention are expressed in IC$_{50}$, and as an illustration the range of IC$_{50}$'s of the compounds in table 1 are between 0.1 nanomolar to 3 micromolar concentrations.

For example, on the protocol 4, the compound No. 7 of table 1 shows an IC$_{50}$ of 0.046 µM, the compound No. 12 of table 1 shows an IC$_{50}$ of 0.0003 µM, the compound No. 21 of table 1 shows an IC$_{50}$ of 0.005 µM, the compound No. 35 of table 1 shows an IC$_{50}$ of 0.012 µM.

Formulation Example (1) Tablets

The ingredients below were mixed by an ordinary method and compressed by using a conventional apparatus.

| Compound of Example 1 | 30 mg |
|---|---|
| Crystalline cellulose | 60 mg |
| Corn starch | 100 mg |
| Lactose | 200 mg |
| Magnesium stearate | 4 mg |

(2) Soft Capsules

The ingredients below were mixed by an ordinary method and filled in soft capsules.

| Compound of Example 1 | 30 mg |
|---|---|
| Olive oil | 300 mg |
| Lecithin | 20 mg |

(1) Parenteral Preparations

The ingredients below were mixed by an ordinary method to prepare injections contained in a 1 ml ampoule.

| Compound of Example 1 | 3 mg |
|---|---|
| Sodium chloride | 4 mg |
| Distilled water for injection | 1 ml |

Industrial Applicability

The compounds of the present invention have GSK3β inhibitory activity and are useful as an active ingredient of a medicament for preventive and/or therapeutic treatment of diseases caused by abnormal activity of GSK3β and more particularly of neurodegenerative diseases.

What is claimed is:
1. A compound of formula (I):

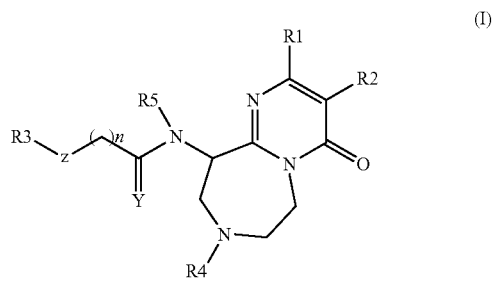

wherein:
Y represents two hydrogen atoms, a sulphur atom, an oxygen atom or a C$_{1-2}$ alkyl group and a hydrogen atom;
z represents a bond, an oxygen atom, a nitrogen atom substituted by a hydrogen atom or a C$_{1-3}$ alkyl group, a sulphur atom, a methylene group optionally substituted by one or two groups chosen from a C$_{1-6}$ alkyl group, a hydroxyl group, a C$_{1-6}$ alkoxy group, a C$_{1-2}$ perhalogenated alkyl group or an amino group;
R1 represents a 2, 3 or 4-pyridine ring or a 2, 4 or 5-pyrimidine ring, the ring being optionally substituted by a C$_{1-6}$ alkyl group, a C$_{1-6}$ alkoxy group or a halogen atom;
R2 represents a hydrogen atom, a C$_{1-6}$ alkyl group or a halogen atom;
R3 represents a benzene ring or a naphthalene ring; the rings being optionally substituted by 1 to 4 substituents selected from a C$_{1-6}$ alkyl group, a halogen atom, a C$_{1-2}$ perhalogenated alkyl group, a C$_{1-3}$ halogenated alkyl group, a hydroxyl group, a C$_{1-6}$ alkoxy group, a C$_{1-2}$ perhalogenated alkoxy group, a C$_{1-6}$ alkylsulfonyl group, a nitro, a cyano, an amino, a C$_{1-6}$ monoalkylamino group, a C$_{2-12}$ dialkylamino group, an acetoxy group or an aminosulfonyl group, a 4-15 membered heterocyclic group, this group being optionally substituted by a C$_{1-6}$ alkyl group, a halogen atom, a C$_{1-2}$ perhalogenated alkyl group, a C$_{1-3}$ halogenated alkyl group, a hydroxyl group, or a C$_{1-6}$ alkoxy group;
R4 represents a hydrogen atom; a C$_{1-6}$ alkyl group; a benzyl group, a phenethyl group, a benzyloxycarbonyl group, a C$_{1-4}$ alkoxy carbonyl group, a benzene group, a naphthalene group, a 5,6,7,8-tetrahydronaphthalene group, a benzenesulfonyl group, a benzoyl group, a 4-15 membered heterocyclic group, the above-mentioned group being optionally substituted by 1 to 4 substituents selected from a halogen atom, a hydroxyl group, a C$_{1-4}$ alkoxy group, a C$_{1-2}$ perhalogenated alkyl group, a C$_{1-6}$ alkyl group, a benzene group, a halogen atom, a C$_{1-3}$ halogenated alkyl group, a nitro, a cyano, an amino, a $C_{1-6}$ monoalkylamino group or a $C_{2-10}$ dialkylamino group;

R5 represents a hydrogen atom or a $C_{1-6}$ alkyl group; and n represents 0 to 3;

or a salt thereof.

2. The compound according to claim 1, wherein

Y represents an oxygen atom or two hydrogen atoms;

z represents a bond;

R1 represents an unsubstituted 4-pyridine ring or unsubstituted 4-pyrimidine ring;

R2 represents an hydrogen atom;

R3 represents a benzene group optionally substituted by 1 to 4 substituents selected from a halogen atom, a $C_{1-2}$ perhalogenated alkyl group, a $C_{1-6}$ alkoxy group, an amino, a pyrazole group, and an oxadiazole group, the oxadiazole group and the pyrazole group being optionally substituted by 1 to 4 substituents selected from a $C_{1-6}$ alkyl group;

R4 represents an hydrogen atom, a $C_{1-6}$ alkyl group, a $COO(C_{1-4}$-alkyl) group, or a phenyl group, these group being eventually substituted by 1 to 3 halogen; and n represents 0;

or a salt thereof.

3. The compound according to claim 1, selected from the group consisting of:

(+/−)-9-(4-Chloro-2-methoxy-benzoylamino)-4-oxo-2-pyrimidin-4-yl-5,6,8,9-tetrahydro-4H-1,4a,7-triaza-benzocycloheptene-7-carboxylic acid ethyl ester;

(+/−)-4-Chloro-2-methoxy-N-(4-oxo-2-pyrimidin-4-yl-4,5,6,7,8,9-hexahydro-1,4a,7-triaza-benzocyclohepten-9-yl)-benzamide;

(+/−)-4-Chloro-2-methoxy-N-(7-methyl-4-oxo-2-pyrimidin-4-yl-4,5,6,7,8,9-hexahydro-1,4a,7-triaza-benzocyclohepten-9-yl)-benzamide;

(+/−)-4-Chloro-N-[7-(4-fluoro-phenyl)-4-oxo-2-pyrimidin-4-yl-4,5,6,7,8,9-hexahydro-1,4a,7-triaza-benzocyclohepten-9-yl]-2-methoxy-benzamide;

(+/−)-4-Chloro-N-(7-cyclopropylmethyl-4-oxo-2-pyrimidin-4-yl-4,5,6,7,8,9-hexahydro-1,4a,7-triaza-benzocyclohepten-9-yl)-2-methoxy-benzamide;

(+/−)-4-Chloro-N-(7-isopropyl-4-oxo-2-pyrimidin-4-yl-4,5,6,7,8,9-hexahydro-1,4a,7-triaza-benzocyclohepten-9-yl)-2-methoxy-benzamide;

(+/−)-4-Chloro-N-(7-cyclopentyl-4-oxo-2-pyrimidin-4-yl-4,5,6,7,8,9-hexahydro-1,4a,7-triaza-benzocyclohepten-9-yl)-2-methoxy-benzamide;

(+/−)-4-Fluoro-2-methoxy-N-(4-oxo-2-pyrimidin-4-yl-4,5,6,7,8,9-hexahydro-1,4a,7-triaza-benzocyclohepten-9-yl)-benzamide;

(+/−)-2,4-Dimethoxy-N-(4-oxo-2-pyrimidin-4-yl-4,5,6,7,8,9-hexahydro-1,4a,7-triaza-benzocyclohepten-9-yl)-benzamide;

(+/−)-4-Chloro-2-methoxy-N-(4-oxo-2-pyridin-4-yl-4,5,6,7,8,9-hexahydro-1,4a,7-triaza-benzocyclohepten-9-yl)-benzamide;

(−)-4-Chloro-2-methoxy-N-(4-oxo-2-pyrimidin-4-yl-4,5,6,7,8,9-hexahydro-1,4a,7-triaza-benzocyclohepten-9-yl)-benzamide;

(+)-4-Chloro-2-methoxy-N-(4-oxo-2-pyrimidin-4-yl-4,5,6,7,8,9-hexahydro-1,4a,7-triaza-benzocyclohepten-9-yl)-benzamide;

(+/−)-9-(4-Methoxy-benzylamino)-4-oxo-2-pyrimidin-4-yl-5,6,8,9-tetrahydro-4H-1,4a,7-triaza-benzocycloheptene-7-carboxylic acid ethyl ester;

(+/−)-9-(2,4-Dimethoxy-benzylamino)-4-oxo-2-pyrimidin-4-yl-5,6,8,9-tetrahydro-4H-1,4a,7-triaza-benzocycloheptene-7-carboxylic acid ethyl ester;

(−)-4-Chloro-2-methoxy-N-(7-methyl-4-oxo-2-pyrimidin-4-yl-4,5,6,7,8,9-hexahydro-1,4a,7-triaza-benzocyclohepten-9-yl)-benzamide;

(+)-4-Chloro-2-methoxy-N-(7-methyl-4-oxo-2-pyrimidin-4-yl-4,5,6,7,8,9-hexahydro-1,4a,7-triaza-benzocyclohepten-9-yl)-benzamide;

(+/−)-9-(2,3-Dimethoxy-benzoylamino)-4-oxo-2-pyrimidin-4-yl-5,6,8,9-tetrahydro-4H-1,4a,7-triaza-benzocycloheptene-7-carboxylic acid ethyl ester;

(+/−)-9-(2-Methoxy-4-trifluoromethyl-benzoylamino)-4-oxo-2-pyrimidin-4-yl-5,6,8,9-tetrahydro-4H-1,4a,7-triaza-benzocycloheptene-7-carboxylic acid ethyl ester;

(+/−)-9-(4-Bromo-benzoylamino)-4-oxo-2-pyrimidin-4-yl-5,6,8,9-tetrahydro-4H-1,4a,7-triaza-benzocycloheptene-7-carboxylic acid ethyl ester;

(+/−)-9-(4-Fluoro-2-trifluoromethyl-benzoylamino)-4-oxo-2-pyrimidin-4-yl-5,6,8,9-tetrahydro-4H-1,4a,7-triaza-benzocycloheptene-7-carboxylic acid ethyl ester;

(+/−)-9-(2-Methoxy-benzoylamino)-4-oxo-2-pyrimidin-4-yl-5,6,8,9-tetrahydro-4H-1,4a,7-triaza-benzocycloheptene-7-carboxylic acid ethyl ester;

(+/−)-2-Methoxy-N-(4-oxo-2-pyrimidin-4-yl-4,5,6,7,8,9-hexahydro-1,4a,7-triaza-benzocyclohepten-9-yl)-benzamide;

(+/−)-5-Bromo-2-methoxy-N-(4-oxo-2-pyrimidin-4-yl-4,5,6,7,8,9-hexahydro-1,4a,7-triaza-benzocyclohepten-9-yl)-benzamide;

(+/−)-2,3-Dimethoxy-N-(4-oxo-2-pyrimidin-4-yl-4,5,6,7,8,9-hexahydro-1,4a,7-triaza-benzocyclohepten-9-yl)-benzamide;

(+/−)-9-Benzylamino-4-oxo-2-pyrimidin-4-yl-5,6,8,9-tetrahydro-4H-1,4a,7-triaza-benzocycloheptene-7-carboxylic acid ethyl ester;

(+/−)-2,3-Dimethoxy-N-(7-methyl-4-oxo-2-pyrimidin-4-yl-4,5,6,7,8,9-hexahydro-1,4a,7-triaza-benzocyclohepten-9-yl)-benzamide;

(+/−)-9-Benzylamino-2-pyrimidin-4-yl-6,7,8,9-tetrahydro-5H-1,4a,7-triaza-benzocyclohepten-4-one;

(+/−)-9-[4-(1-Methyl-1H-pyrazol-4-yl)-benzoylamino]-4-oxo-2-pyrimidin-4-yl-5,6,8,9-tetrahydro-4H-1,4a,7-triaza-benzocycloheptene-7-carboxylic acid ethyl ester;

(+/−)-4-Amino-5-chloro-2-methoxy-N-(4-oxo-2-pyrimidin-4-yl-4,5,6,7,8,9-hexahydro-1,4a,7-triaza-benzocyclohepten-9-yl)-benzamide;

(+/−)-5-Bromo-2-methoxy-N-(7-methyl-4-oxo-2-pyrimidin-4-yl-4,5,6,7,8,9-hexahydro-1,4a,7-triaza-benzocyclohepten-9-yl)-benzamide;

(+/−)-5-Chloro-2-methoxy-N-(7-methyl-4-oxo-2-pyrimidin-4-yl-4,5,6,7,8,9-hexahydro-1,4a,7-triaza-benzocyclohepten-9-yl)-benzamide;

(+/−)-5-Chloro-2-methoxy-N-(4-oxo-2-pyrimidin-4-yl-4,5,6,7,8,9-hexahydro-1,4a,7-triaza-benzocyclohepten-9-yl)-benzamide;

(+/−)-9-(2,4-Dimethoxy-benzoylamino)-4-oxo-2-pyridin-4-yl-5,6,8,9-tetrahydro-4H-1,4a,7-triaza-benzocycloheptene-7-carboxylic acid ethyl ester;

(+/−)-9-(5-Chloro-2-methoxy-benzoylamino)-4-oxo-2-pyridin-4-yl-5,6,8,9-tetrahydro-4H-1,4a,7-triaza-benzocycloheptene-7-carboxylic acid ethyl ester;

(+/−)-9-(4-Fluoro-2-methoxy-benzoylamino)-4-oxo-2-pyridin-4-yl-5,6,8,9-tetrahydro-4H-1,4a,7-triaza-benzocycloheptene-7-carboxylic acid ethyl ester;

(+/−)-9-[(4-Chloro-2-methoxy-benzoyl)-methyl-amino]-4-oxo-2-pyridin-4-yl-5,6,8,9-tetrahydro-4H-1,4a,7-triaza-benzocycloheptene-7-carboxylic acid ethyl ester;

(+/−)-2-Methoxy-4-(5-methyl-[1,2,4]oxadiazol-3-yl)-N-(4-oxo-2-pyrimidin-4-yl-4,5,6,7,8,9-hexahydro-1,4a,7-triaza-benzocyclohepten-9-yl)-benzamide;

(+/−)-2-Methoxy-4-(5-methyl-[1,2,4]oxadiazol-3-yl)-N-(7-methyl-4-oxo-2-pyrimidin-4-yl-4,5,6,7,8,9-hexahydro-1,4a,7-triaza-benzocyclohepten-9-yl)-benzamide;

(+/−)-4-Fluoro-2-methoxy-N-(7-methyl-4-oxo-2-pyridin-4-yl-4,5,6,7,8,9-hexahydro-1,4a,7-triaza-benzocyclohepten-9-yl)-benzamide;

(+/−)-N-(7-Isopropyl-4-oxo-2-pyridin-4-yl-4,5,6,7,8,9-hexahydro-1,4a,7-triaza-benzocyclohepten-9-yl)-2-methoxy-benzamide;

(+/−)-2-Methoxy-N-(4-oxo-2-pyridin-4-yl-4,5,6,7,8,9-hexahydro-1,4a,7-triaza-benzocyclohepten-9-yl)-benzamide;

(+/−)-4-Chloro-N-(7-cyclopropylmethyl-4-oxo-2-pyridin-4-yl-4,5,6,7,8,9-hexahydro-1,4a,7-triaza-benzocyclohepten-9-yl)-2-methoxy-benzamide;

(+/−)-2-Methoxy-N-(4-oxo-2-pyridin-4-yl-4,5,6,7,8,9-hexahydro-1,4a,7-triaza-benzocyclohepten-9-yl)-4-trifluoromethyl-benzamide;

(+/−)-N-(7-Isopropyl-4-oxo-2-pyridin-4-yl-4,5,6,7,8,9-hexahydro-1,4a,7-triaza-benzocyclohepten-9-yl)-2-methoxy-4-trifluoromethyl-benzamide;

(+/−)-N-(7-Cyclopropylmethyl-4-oxo-2-pyridin-4-yl-4,5,6,7,8,9-hexahydro-1,4a,7-triaza-benzocyclohepten-9-yl)-2,5-dimethoxy-benzamide;

((+/−)-2,5-Dimethoxy-N-(4-oxo-2-pyridin-4-yl-4,5,6,7,8,9-hexahydro-1,4a,7-triaza-benzocyclohepten-9-yl)-benzamide;

(+/−)-4-Fluoro-N-(4-oxo-2-pyridin-4-yl-4,5,6,7,8,9-hexahydro-1,4a,7-triaza-benzocyclohepten-9-yl)-2-trifluoromethyl-benzamide;

(+/−)-5-Chloro-2-methoxy-N-(4-oxo-2-pyridin-4-yl-4,5,6,7,8,9-hexahydro-1,4a,7-triaza-benzocyclohepten-9-yl)-benzamide;

(+/−)-4-Fluoro-N-(7-methyl-4-oxo-2-pyridin-4-yl-4,5,6,7,8,9-hexahydro-1,4a,7-triaza-benzocyclohepten-9-yl)-2-trifluoromethyl-benzamide; and (+/−)-N-(7-Benzyl-4-oxo-2-pyridin-4-yl-4,5,6,7,8,9-hexahydro-1,4a,7-triaza-benzocyclohepten-9-yl)-5-chloro-2-methoxy-benzamide;

or a salt thereof.

4. A pyrimidone derivative represented by formula (III) (XI), or (XII):

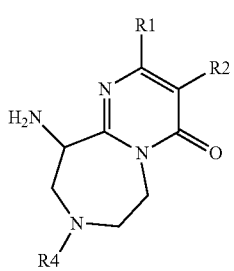

(III)

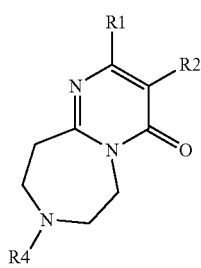

(XI)

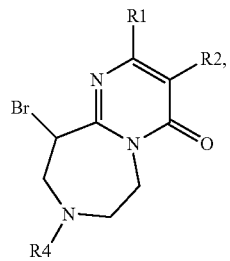

(XII)

wherein R1, R2, and R4 are as defined for the compound of formula (I) according to claim 1.

5. A pharmaceutical composition comprising a compound of formula (I) according to claim 1 or a pharmaceutically acceptable salt thereof, and one or more pharmaceutical additives.

6. A pharmaceutical composition comprising a compound of formula (I) according to claim 2 or a pharmaceutically acceptable salt thereof, and one or more pharmaceutical additives.

7. A pharmaceutical composition comprising a compound of formula (I) according to claim 3 or a pharmaceutically acceptable salt thereof, and one or more pharmaceutical additives.

8. A method of treating a neurodegenerative disease in a patient comprising administering to said patient a therapeutically effective amount of a compound of formula (I) according to claim 1 or a pharmaceutically acceptable salt thereof; wherein said neurodegenerative disease is selected from the group consisting of Alzheimer's disease, Parkinson's disease, tauopathies, vascular dementia; acute stroke, traumatic injuries; cerebrovascular accidents, brain cord trauma, spinal cord trauma; peripheral neuropathies; retinopathies and glaucoma.

9. A method of treating a disease in a patient, said disease selected from the group consisting of non-insulin dependent diabetes; obesity; manic depressive illness; schizophrenia; and cancers, wherein said cancer is selected from the group consisting of breast cancer, non-small cell lung carcinoma, thyroid cancer, T or B-cell leukemia and virus-induced tumors; comprising administering to said patient a therapeutically effective amount of a compound of formula (I) according to claim 1 or a pharmaceutically acceptable salt thereof.

10. A method of treating malaria in a patient, comprising administering to said patient a therapeutically effective amount of a compound of formula (I) according to claim 1 or a pharmaceutically acceptable salt thereof.

11. A method of treating Pemphigus vulgaris in a patient, comprising administering to said patient a therapeutically effective amount of a compound of formula (I) according to claim 1 or a pharmaceutically acceptable salt thereof.

12. A process for the preparation of a compound of formula (I) according to claim 1 comprising:
reacting a compound of formula (III):

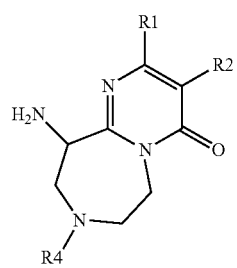

(III)

with a compound of formula (II):
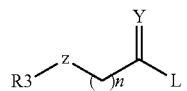
(II)
wherein z, R1, R2, R3, R4, Y and n are as defined in claim 1, and L represents a leaving group.
* * * * *